(12) United States Patent
McCaffrey et al.

(10) Patent No.: US 10,898,656 B2
(45) Date of Patent: Jan. 26, 2021

(54) NEEDLE MECHANISM MODULE FOR DRUG DELIVERY DEVICE

(71) Applicant: INSULET CORPORATION, Acton, MA (US)

(72) Inventors: Maureen McCaffrey, Boston, MA (US); Ian McLaughlin, Boxboro, MA (US)

(73) Assignee: INSULET CORPORATION, Acton, MA (US)

( * ) Notice: Subject to any disclaimer, the term of this patent is extended or adjusted under 35 U.S.C. 154(b) by 221 days.

(21) Appl. No.: 16/140,178

(22) Filed: Sep. 24, 2018

(65) Prior Publication Data

US 2019/0091417 A1 Mar. 28, 2019

Related U.S. Application Data

(60) Provisional application No. 62/563,327, filed on Sep. 26, 2017.

(51) Int. Cl.
*A61M 5/32* (2006.01)
*A61M 5/142* (2006.01)
*A61M 5/158* (2006.01)
*A61M 5/168* (2006.01)

(52) U.S. Cl.
CPC ...... *A61M 5/3287* (2013.01); *A61M 5/14244* (2013.01); *A61M 5/14248* (2013.01); *A61M 5/158* (2013.01); *A61M 5/168* (2013.01); *A61M 2005/14252* (2013.01); *A61M 2005/1583* (2013.01); *A61M 2005/1585* (2013.01)

(58) Field of Classification Search
CPC ............ A61M 5/3287; A61M 5/14244; A61M 5/14248; A61M 5/158; A61M 2005/1585; A61M 2005/1583; A61M 5/168; A61M 2005/14252
See application file for complete search history.

(56) References Cited

U.S. PATENT DOCUMENTS

| 303,013 A | 8/1884 | Horton |
|---|---|---|
| 306,691 A | 10/1884 | Johnson |
| 315,727 A | 4/1885 | Church |

(Continued)

FOREIGN PATENT DOCUMENTS

| DE | 420595 A | 7/1993 |
|---|---|---|
| DE | 19723648 C1 | 8/1998 |

(Continued)

OTHER PUBLICATIONS

US 5,954,699 A, 09/1999, Jost et al. (withdrawn)

(Continued)

*Primary Examiner* — Amber R Stiles
(74) *Attorney, Agent, or Firm* — Kacvinsky Daisak Bluni PLLC

(57) ABSTRACT

A needle mechanism module for automatically inserting a fluid path into a patient for drug delivery is provided. The needle mechanism module can be a component of a wearable drug delivery device. The needle mechanism module can insert a needle and cannula into the patient responsive to activation of the drug delivery device by a user. After insertion, the needle can be automatically retracted, leaving only the cannula in the patient. As a result, discomfort of the user is reduced.

20 Claims, 19 Drawing Sheets

(56) References Cited

U.S. PATENT DOCUMENTS

| | | |
|---|---|---|
| 405,524 A | 6/1889 | Benton |
| 410,817 A | 9/1889 | Weeks, Jr. |
| 2,667,986 A | 2/1954 | Perelson |
| 3,631,847 A | 1/1972 | Hobbs |
| 3,792,703 A | 2/1974 | Moorehead |
| 3,812,843 A | 5/1974 | Wootten et al. |
| 3,841,328 A | 10/1974 | Jensen |
| 3,885,662 A | 5/1975 | Schaefer |
| 4,067,000 A | 1/1978 | Carlson |
| 4,151,845 A | 5/1979 | Clemens |
| 4,152,098 A | 5/1979 | Moody et al. |
| 4,193,397 A | 3/1980 | Tucker et al. |
| 4,211,998 A | 7/1980 | Junginger et al. |
| 4,231,019 A | 10/1980 | Junginger et al. |
| 4,268,150 A | 5/1981 | Chen |
| 4,342,311 A | 8/1982 | Whitney et al. |
| 4,346,385 A | 8/1982 | Schiavone et al. |
| 4,364,385 A | 12/1982 | Lossef |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopf |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| 4,855,746 A | 8/1989 | Stacy |
| 4,858,619 A | 8/1989 | Toth |
| 4,871,351 A | 10/1989 | Feingold |
| 4,882,600 A | 11/1989 | Van de Moere |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,944,659 A | 7/1990 | Labbe et al. |
| 4,969,874 A | 11/1990 | Michel et al. |
| 4,973,998 A | 11/1990 | Gates |
| 4,994,047 A | 2/1991 | Walker et al. |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,125,415 A | 6/1992 | Bell |
| 5,176,662 A | 1/1993 | Bartholomew et al. |
| 5,178,609 A | 1/1993 | Ishikawa |
| 5,189,609 A | 2/1993 | Tivig et al. |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,244,463 A | 9/1993 | Cordner, Jr. et al. |
| 5,245,447 A | 9/1993 | Stemmle |
| 5,254,096 A | 10/1993 | Rondelet et al. |
| 5,257,980 A | 11/1993 | Van Antwerp et al. |
| 5,261,884 A | 11/1993 | Stern et al. |
| 5,281,202 A | 1/1994 | Weber et al. |
| 5,308,335 A | 5/1994 | Ross et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A | 9/1994 | Elson |
| 5,364,342 A | 11/1994 | Beuchat et al. |
| 5,411,480 A | 5/1995 | Kriesel |
| 5,433,710 A | 7/1995 | VanAntwerp et al. |
| 5,452,033 A | 9/1995 | Balling et al. |
| 5,492,534 A | 2/1996 | Athayde et al. |
| 5,503,628 A | 4/1996 | Fetters et al. |
| 5,505,709 A | 4/1996 | Funderburk et al. |
| 5,507,288 A | 4/1996 | Bocker et al. |
| 5,514,096 A | 5/1996 | Hiejima |
| 5,533,389 A | 7/1996 | Kamen et al. |
| 5,545,152 A | 8/1996 | Funderburk et al. |
| 5,573,342 A | 11/1996 | Patalano |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,613,956 A | 3/1997 | Patterson et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,665,065 A | 9/1997 | Colman et al. |
| 5,665,070 A | 9/1997 | McPhee |
| 5,685,859 A | 11/1997 | Komerup |
| 5,693,018 A | 12/1997 | Kriesel et al. |
| 5,695,490 A | 12/1997 | Flaherty et al. |
| 5,702,363 A | 12/1997 | Flaherty |
| 5,704,520 A | 1/1998 | Gross |
| 5,716,343 A | 2/1998 | Kriesel et al. |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,764,159 A | 6/1998 | Neftel |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | McPhee |
| 5,800,420 A | 9/1998 | Gross et al. |
| 5,810,015 A | 9/1998 | Flaherty |
| 5,814,020 A | 9/1998 | Gross |
| 5,840,063 A | 11/1998 | Flaherty |
| 5,845,218 A | 12/1998 | Altschul |
| 5,848,990 A | 12/1998 | Cirelli et al. |
| 5,848,991 A | 12/1998 | Gross et al. |
| 5,851,197 A | 12/1998 | Marano et al. |
| 5,858,005 A | 1/1999 | Kriesel |
| 5,858,239 A | 1/1999 | Kenley et al. |
| 5,865,806 A | 2/1999 | Howell |
| 5,871,470 A | 2/1999 | McWha |
| 5,875,393 A | 2/1999 | Altschul et al. |
| 5,878,539 A | 3/1999 | Grubb |
| 5,885,659 A | 3/1999 | Takahashi et al. |
| 5,885,808 A | 3/1999 | Spooner et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,921,419 A | 7/1999 | Niedospial, Jr. et al. |
| 5,931,814 A | 8/1999 | Alex et al. |
| 5,935,099 A | 8/1999 | Peterson et al. |
| 5,954,058 A | 9/1999 | Flaherty |
| 5,954,694 A | 9/1999 | Sunseri |
| 5,957,859 A | 9/1999 | Rosenfeld |
| 5,957,890 A | 9/1999 | Mann et al. |
| 5,961,492 A | 10/1999 | Kriesel et al. |
| 5,965,848 A | 10/1999 | Altschul et al. |

(56) References Cited

U.S. PATENT DOCUMENTS

| | | | |
|---|---|---|---|
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,024,539 A | 2/2000 | Blomquist |
| 6,050,978 A | 4/2000 | Orr et al. |
| 6,071,292 A | 6/2000 | Makower et al. |
| 6,090,092 A | 7/2000 | Fowles et al. |
| 6,126,637 A | 10/2000 | Kriesel et al. |
| 6,144,847 A | 11/2000 | Altschul et al. |
| 6,152,898 A | 11/2000 | Olsen |
| 6,174,300 B1 | 1/2001 | Kriesel et al. |
| 6,190,359 B1 | 2/2001 | Heruth |
| 6,200,338 B1 | 3/2001 | Solomon et al. |
| 6,206,850 B1 | 3/2001 | ONeil |
| 6,244,776 B1 | 6/2001 | Wiley |
| 6,309,370 B1 | 10/2001 | Haim et al. |
| 6,363,609 B1 | 4/2002 | Pickren |
| 6,375,639 B1 | 4/2002 | Duplessie et al. |
| 6,475,196 B1 | 11/2002 | Vachon |
| 6,520,936 B1 | 2/2003 | Mann |
| 6,527,744 B1 | 3/2003 | Kriesel et al. |
| 6,569,125 B2 | 5/2003 | Jepson et al. |
| 6,572,542 B1 | 6/2003 | Houben et al. |
| 6,572,585 B2 | 6/2003 | Choi |
| 6,666,852 B2 | 12/2003 | Niedospial, Jr. |
| 6,699,221 B2 | 3/2004 | Vaillancourt |
| 6,740,059 B2 | 5/2004 | Flaherty |
| 6,883,778 B1 | 4/2005 | Newton et al. |
| 7,008,404 B2 | 3/2006 | Nakajima |
| 7,018,360 B2 | 3/2006 | Flaherty et al. |
| 7,025,744 B2 | 4/2006 | Utterberg et al. |
| 7,128,727 B2 | 10/2006 | Flaherty et al. |
| 7,144,384 B2 | 12/2006 | Gorman et al. |
| 7,160,272 B1 | 1/2007 | Eyal et al. |
| 7,291,133 B1 | 11/2007 | Kindler et al. |
| 7,303,549 B2 | 12/2007 | Flaherty et al. |
| 7,918,825 B2 | 4/2011 | O'Connor et al. |
| 9,402,950 B2 | 8/2016 | Diianni et al. |
| 2001/0053895 A1 | 12/2001 | Vaillancourt |
| 2002/0010423 A1 | 1/2002 | Gross et al. |
| 2002/0032374 A1 | 3/2002 | Holker et al. |
| 2002/0066715 A1 | 6/2002 | Niedospial |
| 2002/0123740 A1 | 9/2002 | Flaherty et al. |
| 2003/0163097 A1 | 8/2003 | Fleury et al. |
| 2004/0010207 A1 | 1/2004 | Flaherty et al. |
| 2004/0064088 A1 | 4/2004 | Gorman et al. |
| 2004/0088224 A1 | 5/2004 | Mukai |
| 2004/0092865 A1 | 5/2004 | Flaherty et al. |
| 2004/0116847 A1 | 6/2004 | Wall |
| 2004/0203357 A1 | 10/2004 | Nassimi |
| 2005/0020980 A1 | 1/2005 | Inoue et al. |
| 2005/0187524 A1 | 8/2005 | Willis et al. |
| 2005/0203461 A1 | 9/2005 | Flaherty et al. |
| 2005/0238507 A1 | 10/2005 | Diianni et al. |
| 2005/0258581 A1 | 11/2005 | Tanaka |
| 2006/0134323 A1 | 6/2006 | O'Brien |
| 2006/0155210 A1 | 7/2006 | Beckman et al. |
| 2006/0178633 A1 | 8/2006 | Garibotto et al. |
| 2006/0204535 A1 | 9/2006 | Johnson |
| 2006/0253085 A1 | 11/2006 | Geismar et al. |
| 2006/0282290 A1 | 12/2006 | Flaherty et al. |
| 2007/0005018 A1 | 1/2007 | Tekbuchava |
| 2007/0025811 A1 | 2/2007 | Wilhelm |
| 2007/0112332 A1 | 5/2007 | Harding et al. |
| 2007/0118405 A1 | 5/2007 | Campbell et al. |
| 2007/0129690 A1 | 6/2007 | Rosenblatt et al. |
| 2007/0173974 A1 | 7/2007 | Lin |
| 2007/0197163 A1 | 8/2007 | Robertson |
| 2007/0282269 A1 | 12/2007 | Carter et al. |
| 2008/0004515 A1 | 1/2008 | Jennewine |
| 2008/0006500 A1 | 1/2008 | Spahr |
| 2008/0051738 A1 | 2/2008 | Griffin |
| 2008/0065000 A1 | 3/2008 | Bidinger et al. |
| 2008/0065050 A1 | 3/2008 | Sparks et al. |
| 2008/0078400 A1 | 4/2008 | Martens et al. |
| 2008/0132880 A1 | 6/2008 | Buchman |
| 2008/0249508 A1 | 10/2008 | Lopez et al. |
| 2008/0287906 A1 | 11/2008 | Burkholz et al. |
| 2009/0062767 A1 | 3/2009 | Van Antwerp et al. |
| 2009/0069787 A1 | 3/2009 | Estes et al. |
| 2009/0099521 A1 | 4/2009 | Gravesen et al. |
| 2009/0124979 A1* | 5/2009 | Raymond ......... A61M 5/14244 604/195 |
| 2009/0198215 A1 | 8/2009 | Chong et al. |
| 2009/0299300 A1 | 12/2009 | Truitt et al. |
| 2010/0137784 A1 | 6/2010 | Cefai et al. |
| 2010/0152658 A1 | 6/2010 | Hanson et al. |
| 2011/0054390 A1 | 3/2011 | Searle et al. |
| 2011/0054399 A1 | 3/2011 | Chong et al. |
| 2011/0144586 A1 | 6/2011 | Michaud et al. |
| 2011/0166512 A1 | 7/2011 | Both et al. |
| 2011/0230833 A1 | 9/2011 | Landman et al. |
| 2011/0251509 A1 | 10/2011 | Beyhan et al. |
| 2011/0316562 A1 | 12/2011 | Cefai et al. |
| 2012/0003093 A1 | 1/2012 | Lischer et al. |
| 2012/0003935 A1 | 1/2012 | Lydon et al. |
| 2012/0010594 A1 | 1/2012 | Holt et al. |
| 2012/0045667 A1 | 2/2012 | Yoneda et al. |
| 2012/0078161 A1 | 3/2012 | Masterson et al. |
| 2012/0238851 A1 | 9/2012 | Kamen et al. |
| 2012/0277668 A1 | 11/2012 | Chawla |
| 2013/0060233 A1 | 3/2013 | O'Connor et al. |
| 2013/0178791 A1 | 7/2013 | Javitt |
| 2013/0317753 A1 | 11/2013 | Kamen et al. |
| 2014/0074033 A1 | 3/2014 | Sonderegger et al. |
| 2014/0127048 A1 | 5/2014 | Diianni et al. |
| 2014/0128839 A1 | 5/2014 | Dilanni et al. |
| 2014/0135880 A1 | 5/2014 | Baumgartner et al. |
| 2014/0316379 A1 | 10/2014 | Sonderegger et al. |
| 2016/0015891 A1 | 1/2016 | Papiorek |
| 2016/0038689 A1 | 2/2016 | Lee et al. |
| 2016/0302054 A1 | 10/2016 | Kimura et al. |
| 2017/0128664 A1 | 5/2017 | Diianni et al. |

FOREIGN PATENT DOCUMENTS

| | | |
|---|---|---|
| DE | 19920896 A1 | 11/2000 |
| EP | 0341049 A2 | 11/1989 |
| EP | 0342947 A2 | 11/1989 |
| EP | 0496305 A2 | 7/1992 |
| EP | 0763369 A1 | 3/1997 |
| EP | 0867196 A2 | 9/1998 |
| EP | 0937475 A2 | 8/1999 |
| EP | 2397181 A1 | 12/2011 |
| EP | 2830499 A1 | 2/2015 |
| GB | 875034 A | 8/1961 |
| GB | 2443261 A | 4/2008 |
| TW | 200740148 A | 10/2007 |
| TW | M452390 U | 5/2013 |
| WO | 8101658 A1 | 6/1981 |
| WO | 8606796 A1 | 11/1986 |
| WO | 9800193 A1 | 1/1998 |
| WO | 9801071 A1 | 1/1998 |
| WO | 9856293 A1 | 12/1998 |
| WO | 9910040 A1 | 3/1999 |
| WO | 9956803 A1 | 11/1999 |
| WO | 9962576 A1 | 12/1999 |
| WO | 0019887 A1 | 4/2000 |
| WO | 0029047 A1 | 5/2000 |
| WO | 0029049 A1 | 5/2000 |
| WO | 0030705 A1 | 6/2000 |
| WO | 0061215 A1 | 10/2000 |
| WO | 0074752 A1 | 12/2000 |
| WO | 0078210 A1 | 12/2000 |
| WO | 0152727 A1 | 7/2001 |
| WO | 0156633 A2 | 8/2001 |
| WO | 0172354 A2 | 10/2001 |
| WO | 0176684 A1 | 10/2001 |
| WO | 2002015954 A1 | 2/2002 |
| WO | 0220073 A2 | 3/2002 |
| WO | 0226282 A2 | 4/2002 |
| WO | 0240083 A2 | 5/2002 |
| WO | 2002068823 | 9/2002 |

(56) References Cited

FOREIGN PATENT DOCUMENTS

| | | | |
|---|---|---|---|
| WO | 03090509 A2 | 11/2003 |
| WO | 2006053007 A2 | 5/2006 |
| WO | 2007064835 A2 | 6/2007 |
| WO | 2008024810 A2 | 2/2008 |
| WO | 20080133702 A1 | 11/2008 |
| WO | 2009098648 A2 | 8/2009 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2013078200 A1 | 5/2013 |
| WO | 2013134486 A2 | 9/2013 |
| WO | 2013149186 A1 | 10/2013 |
| WO | 2013182321 A1 | 12/2013 |
| WO | 2014194183 A2 | 12/2014 |
| WO | 2015061493 A1 | 4/2015 |
| WO | 2015081337 A2 | 6/2015 |
| WO | 2016141082 A1 | 9/2016 |
| WO | 2017205816 A1 | 11/2017 |

OTHER PUBLICATIONS

International Preliminary Report on Patentability dated Oct. 9, 2014, issued in PCT Patent Application No. PCT/US2013/034674, 15 pages.
EPO Search Report dated Nov. 11, 2015, received in corresponding Application No. 13768938.6, 7 pgs.
European Patent Office, "Notification of Transmittal of the ISR and the Written Opinion of the International Searching Authority, or the Declaration," in PCT Application No. PCT/GB2015/050248, dated Jun. 23, 2015, 12 pages.
U.K. Intellectual Property Office, GB Application No. GB 1401591.1, ""Search Report under Section 17(5)"" dated Jul. 9, 2015, 3 pages.
International Preliminary Report on Patentability dated Apr. 9, 2020, issued in PCT Patent Application No. PCT/US2018/052464, 7 pages.
International Search Report for the International Patent Application No. PCT/US03/16640, dated Oct. 3, 2003, 1 page.
User's Guide for Model 508 Insulin Pump, Mini Med, Aug. 2000, 153 pages.
Web-Site Brochure dated Jan. 4, 2000. SOOIL-Homepage. "Portable Insulin Pump". www.sooil.com/product2.htm.
"Web-Site Brochure dated Jan. 4, 2000. SOOIL-Homepage. ""Portable Insulin Pump"".www.sooil.com/product3.htm".
Web-Site Brochure dated Jan. 4, 2000. SOOIL-Homepage. "Portable Insulin Pump". www.sooil.com/product4.htm.
Web-Site Brochure dated Dec. 20, 1999. "The Animas R-1000 Insulin Pump". www .animascorp.com/pump f _ s.html.
"Web-Site Brochure dated Dec. 20, 1999. ""The Animas R-1000 Insulin Pump"" www.animascorp.com/pump_f_f.html".
"Web-Site Brochure dated Jan. 4, 2000. SOOIL-Homepage. ""Ponable Insulin Pump"".www.sooil.com/intro2.htm".
Web-Site Brochure dated Jan. 4, 2000. MiniMed 508. "Doing its job. Naturally." www.minimed.com/tiles/mm113.htm.
"Web-Site Brochure dated Dec. 20, 1999. Applied Medical Technology. ""508 Pump Information"". www.applied-medical.co.uk/508.htm".
"Web-Site Brochure dated Jan. 4, 2000. ""The Glucose Sensor"". www.animascorp.com/sensor f.html".
International Search Report and Written Opinion of PCT/US2018/018901, dated Jun. 8, 2018, 12 pages.
International Search Report and Written Opinion for Application No. PCT/US2017/015601, dated May 16, 2017, 12 pages.
International Search Report and Written Opinion for application No. PCT/US18/52464, dated Jan. 4, 2019, 14 pages.

* cited by examiner

NEEDLE MECHANISM MODULE FOR DRUG DELIVERY DEVICE

CROSS-REFERENCE TO RELATED APPLICATIONS

This application claims the benefit of U.S. Provisional Application No. 62/563,327, filed Sep. 26, 2017, which is incorporated herein by reference in its entirety.

TECHNICAL FIELD

Embodiments generally relate to medication delivery. More particularly, embodiments relate to automatic insertion of a fluid path component into a patient for drug delivery.

BACKGROUND

Conventional on-body or wearable drug delivery devices (e.g., infusion devices or pumps) often require manual insertion of a needle into the user to provide a fluid path from a liquid drug stored in the drug delivery device to the user. Many users dislike the manual needle insertion required by these conventional drug delivery devices. Further, many users may not insert the needle properly, thereby leading to inefficient or improper use of the conventional drug delivery device.

Accordingly, there is a need for a drug delivery device that provides for automatic insertion of a fluid path component into the user that reduces the discomfort of the user while preventing any user error.

DETAILED DESCRIPTION

This disclosure presents various systems, components, and methods related to a drug delivery device and, in particular, a needle mechanism module for automatically inserting and retracting a needle. Each of the systems, components, and methods disclosed herein provides one or more advantages over conventional systems, components, and methods.

Various embodiments include a needle mechanism module for automatically inserting a needle and a cannula into a patient or user and retracting the needle, thereby leaving the cannula in the patient for the delivery of a drug from a wearable or on-body drug delivery device of which the needle mechanism module can be a component.

In various embodiments, the needle mechanism module can insert a fluid path component or portion thereof into a patient automatically for drug delivery. In an on-body delivery system (e.g., a wearable drug delivery system), automatic insertion of the fluid path component into the patient can reduce fear and/or pain that may be experienced by the user and may also minimize user error. The needle mechanism module can further improve patient comfort by retracting the introducer needle and leaving only a soft cannula in the patient. In various embodiments, the needle is never seen by the patient, as it is initially inside the drug delivery device and automatically retracts back into the device upon insertion. The quick action of a spring-loaded insertion mechanism can minimize the amount of time the needle is in the patient and may decrease pain as compared with a manual insertion of a needle. Further, retraction of the needle back into the device provides sharps protection when the drug delivery device is removed from the user. The needle mechanism module can be provided as a standalone component, and so is highly transferable for use in different device designs. Other embodiments are disclosed and described.

Figure 1:
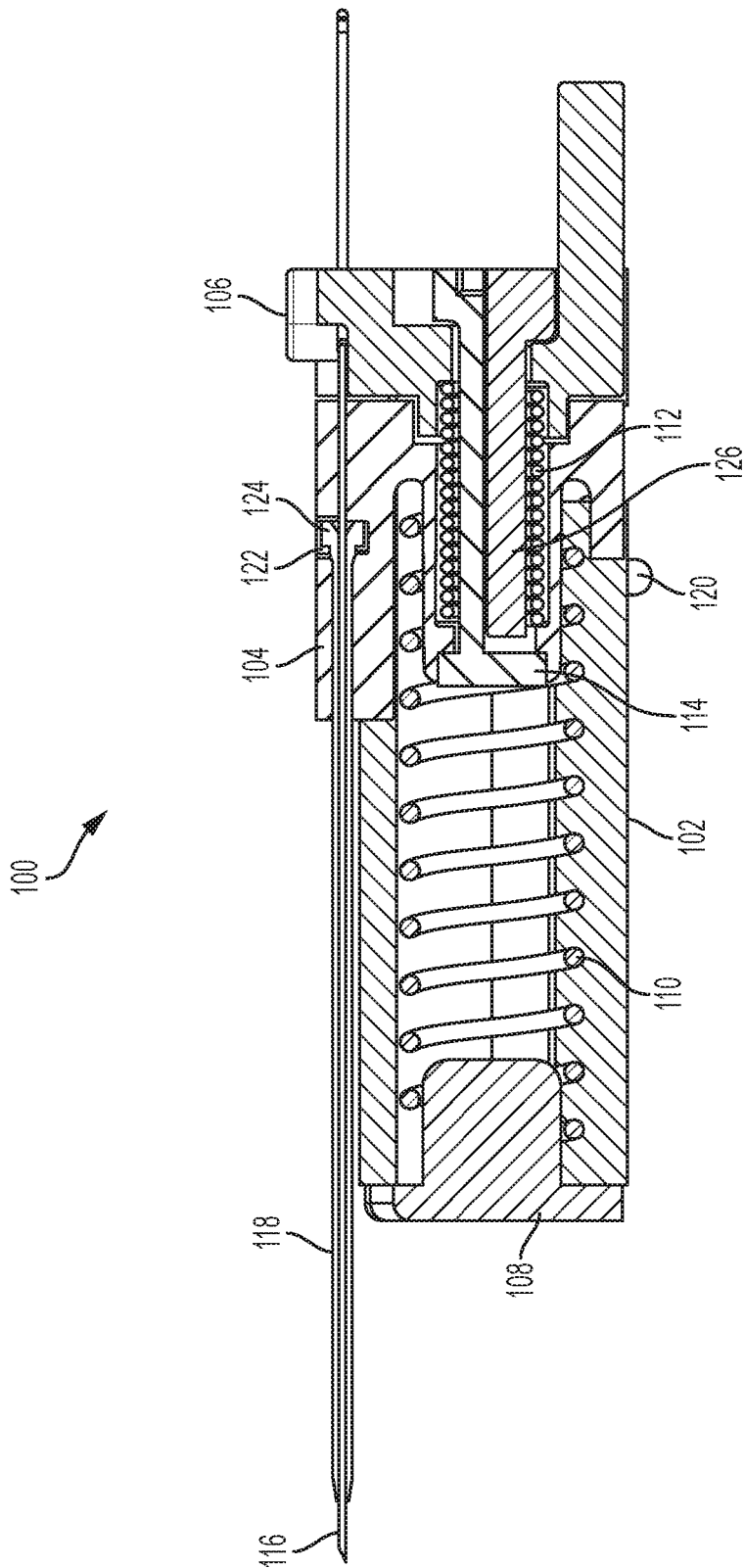
FIG. 1 illustrates a first cross-sectional side view of an exemplary needle mechanism module.

FIG. 1 illustrates a needle mechanism or needle mechanism module 100. The needle mechanism module 100 can be a component or part of a drug delivery device such as, for example, an on-body or wearable drug delivery device. The needle mechanism module 100 can automatically insert a fluid path component into a patient to facilitate drug delivery. In various embodiments, the needle mechanism module 100 can insert and retract an introducer needle and can leave a soft cannula in the patient. The soft cannula and retracted introducer needle can form a portion of the fluid path component coupling a liquid drug stored within the drug delivery device to the patient.

FIG. 1 shows a side cross-sectional view of the needle mechanism module 100. As shown in FIG. 1, the needle mechanism module 100 can include a rail housing component 102, a slide insert component 104, a slide retract component 106, a hard stop component 108, an insert spring 110, a retract spring 112, a tension lock component 114, a needle 116, a cannula 118, a lock component 120, and a rail beam component 126. FIG. 1 illustrates the needle mechanism module 100 prior to activation. That is, FIG. 1 illustrates the needle mechanism module 100 in an initial operational state prior to insertion and retraction of the needle 116.

As shown in FIG. 1, the slide insert 104 and the slide retract 106 are coupled together and spaced apart from the hard stop 108. The hard stop 108 can be positioned at a first end of the rail 102. The slide insert 104 and the slide retract 106 can be positioned at a second, opposite end of the rail 102. The position of the hard stop 108 can be fixed. The slide insert 104 and the slide retract 106 can move along and within the rail 102 when not locked to the position shown in FIG. 1 as described further herein. The insert spring 110 can be an extension spring. The insert spring 110 can be coupled to the hard stop 108 and to the slide insert 104. The insert spring 110 can be configured to be biased so as to draw or bring the slide insert 104 and the slide retract 106 toward the hard stop 108. The lock 120 can be configured to prevent the insert spring 110 from moving the slide insert 104 and the slide retract 106 toward the hard stop 108. As shown in FIG. 1, the lock 120 can be coupled to or positioned adjacent to a portion of the slide insert 104. The arrangement of the lock 120 and the slide insert 104 as shown in FIG. 1 can prevent or block the slide insert 104 (and the coupled slide retract 106) from moving toward the hard stop 108. The rail beam 126, as further described herein, can be coupled to the rail 102 and can restrict downward movement of the tension lock 114 as described herein.

As shown in FIG. 1, the needle 116 (e.g., an introducer needle) and the cannula 118 (e.g., a soft cannula) can be coupled to the slide insert 104. The needle 116 can be positioned inside of the cannula 118 such that the cannula 118 fits over and around a portion of the needle 116. The slide insert 104 can include a pocket 122. An end portion or nail head 124 of the cannula 118 can be positioned within the pocket 122. The end portion or nail head 124 of the cannula 118 and the pocket 122 can be configured to hold or retain the cannula 118. The needle 116 can extend beyond the slide retract 106 as shown. A portion of the needle 116 that extends beyond the slide retract 106 can be a service loop of the needle 116. The service loop of the needle 116 can allow the needle 116 to move forward for insertion (e.g., the service loop of the needle 116 can provide slack for when the needle 116 moves forward in a direction toward the hard stop 108 during insertion). The needle 116 can be coupled to a liquid drug or other therapeutic agent stored by a wearable drug delivery device (e.g., stored in a reservoir). The needle 116 and the cannula 118 can form the fluid path component (or a portion thereof) coupling the liquid drug to the patient. The stored liquid drug can be provided to a patient by way of the needle 116 and the cannula 118 as described further herein.

Figure 2:
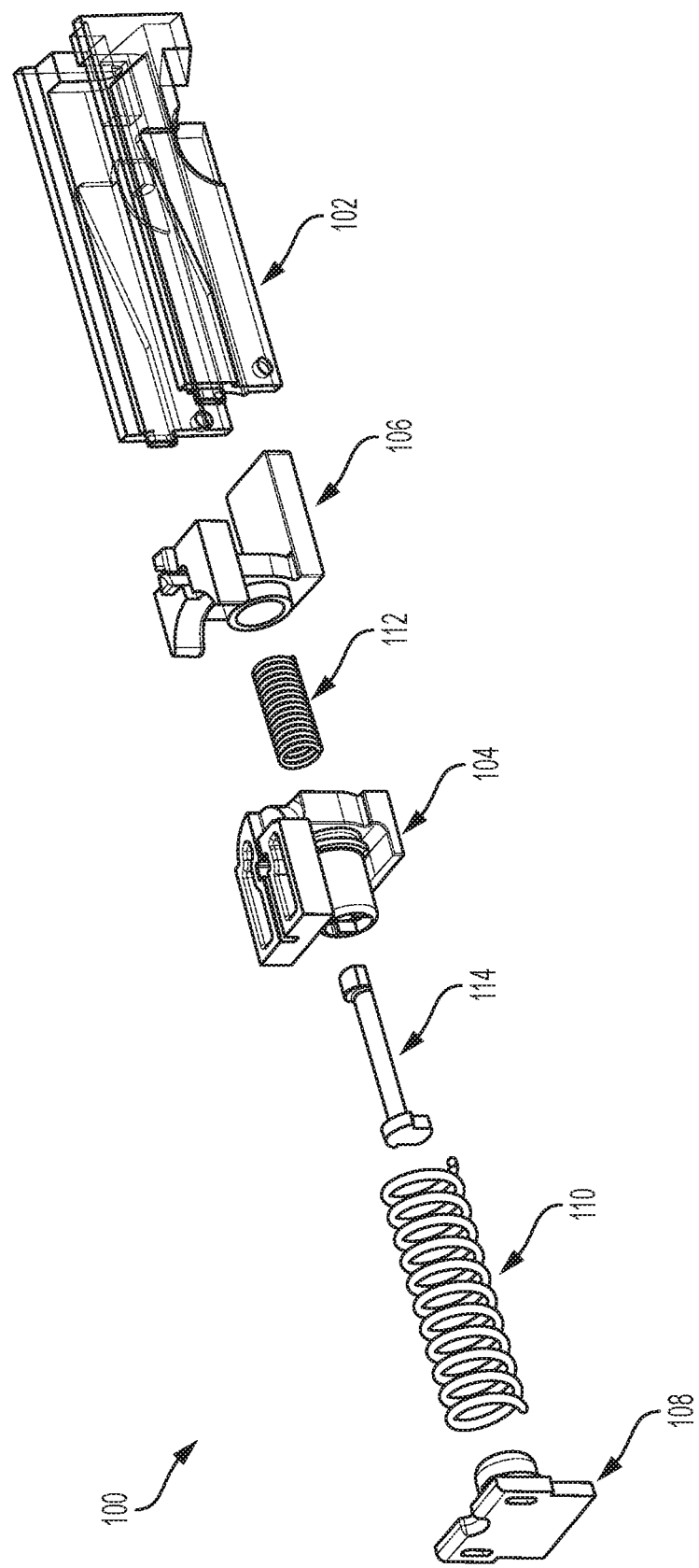
FIG. 2 illustrates an exploded view of a portion of the needle mechanism module depicted in FIG. 1.

FIG. 2 illustrates an exploded view of a portion of the needle mechanism module 100 depicted in FIG. 1. The needle 116 and the cannula 118 are not shown in FIG. 2 for simplicity and clarity. FIG. 2 shows the arrangement of the constituent components of the needle mechanism module 100 described in relation to FIG. 1.

Referring to FIGS. 1 and 2, the hard stop 108 can be attached to a first end of the rail 102. The rail 102 can have an open center area to accommodate the other components of the needle mechanism module 100. When not locked into the position shown in FIG. 1, the slide insert 104 and the slide retract 106 can move along the open area of the rail 102 toward the hard stop 108. The spring 110 can be coupled to the hard stop 108 and the slide insert 104. The tension lock component 114 can be positioned to couple the slide insert 104 to the slide retract 106. Specifically, a first end of the tension lock component 114 can attached or coupled to a center portion of the slide insert 104 and a second, opposite end of the tension lock component 114 can extend beyond the slide retract 106. The second end of the tension lock component 114 can be larger than the portion of the tension lock component 114 that connects the first and second ends of the tension lock component 114. The increased size of the second end of the tension lock component 114, in conjunction with the connection of the first end to the slide insert 104, can keep the slide inset 104 and slide retract 106 coupled closely together as shown.

A portion of the spring 110 can be positioned around the center portion of the slide insert 104. A portion of the center portion of the slide insert 104 can be open along with a portion of a center portion of the slide retract 106. The spring 112 can be positioned within these open areas of the slide insert 104 and the slide retract 106 as shown. The spring 112 can be a compression spring. The tension lock component 114 and the rail beam 126 can be positioned within these open areas as well. The spring 112 can be positioned around the tension lock component 114 and the rail beam 126 as shown.

Figure 3:
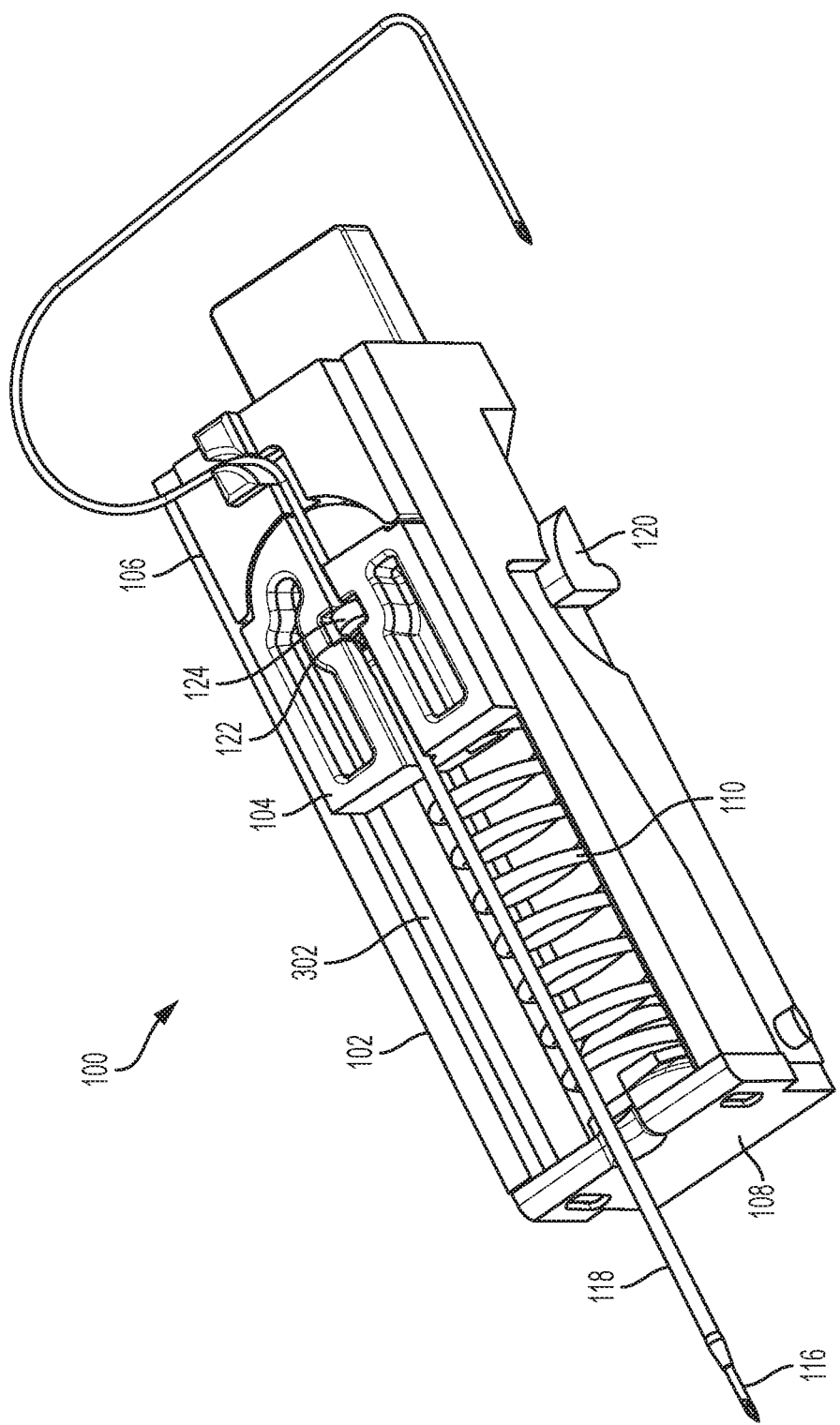
FIG. 3 illustrates an overhead side view of the needle mechanism module depicted in FIG. 1.

FIG. 3 illustrates an overhead side view of the needle mechanism module 100 as depicted in FIG. 1. FIG. 3 furthers shows the arrangement of the constituent components of the needle mechanism module 100 described in relation to FIG. 1. As shown in FIG. 3, the needle 116 can be routed through the slide retract 106 and can extend beyond the slide retract 106. The needle 116 can be shaped as desired to be routed through the drug delivery device to be coupled to the stored liquid drug (e.g., to an outlet of a reservoir storing the liquid drug). Further, the needle 116 can be wrapped around a notch or other feature in the slide retract 106 to allow it to move with the slide retract 106.

Referring to FIGS. 1 and 3, the cannula 118 is positioned around a portion of the needle 116. The nail head 124 of the cannula 118 is directly attached to the slide insert 104. The needle 116 is routed through this portion of the cannula 118 and through the slide insert 104. Accordingly, in various embodiments, the needle 116 is not directly attached to the slide insert 104. The needle 116 can be directly attached to the slide retract 106 (e.g., attached to a notch or other coupling between the slide retract 106 and the needle 116). This arrangement of components and routing of the needle 116 relative to the cannula 118 allows the needle 116 and the cannula 118 to both move together toward the hard stop 108 as the slide insert 104 and the slide retract 106 both move toward the hard stop 108 as further described herein. Further, this arrangement of components and routing of the needle 116 relative to the cannula 118 allows the cannula 118 to be held in a fixed, stationary position when the slide insert 104 is held in a fixed position as the slide retract 106 is moved back away from the hard stop 108, which causes the needle 116 to also move with the slide retract 106 and therefore away from the hard stop 108. As described further herein, this enables the needle 116 and the cannula 118 to both be driven in a first direction to pierce a skin of a user and then to have the needle 116 be retracted out of the user in a second direction, leaving only the cannula 118 coupled to the user.

FIG. 3 also shows the open center area of the rail 102. In particular, FIG. 3 shows a portion of the hard stop 108 extending into the open center of the rail 102 and the spring 110 coupled to the hard stop 108. The slide insert 104 and slide retract 106 can include top portions that rest and can slide along rails 302. In various embodiments, the rail component 102 can be considered to be a housing that is generally rectangularly-shaped with an open center area.

The perimeter of the sides of the open center area can include rails 302 (positioned on either side of the open center area) that the slide insert 104 and the slide retract 106 can rest on and slide along. The rails 302 can be lowered portions of the side walls of the rail component 102 as shown that provides a pathway of movement while allowing the side walls of the rail component 102 to stabilize the slide insert 104 and the slide retract 106.

Figure 4:
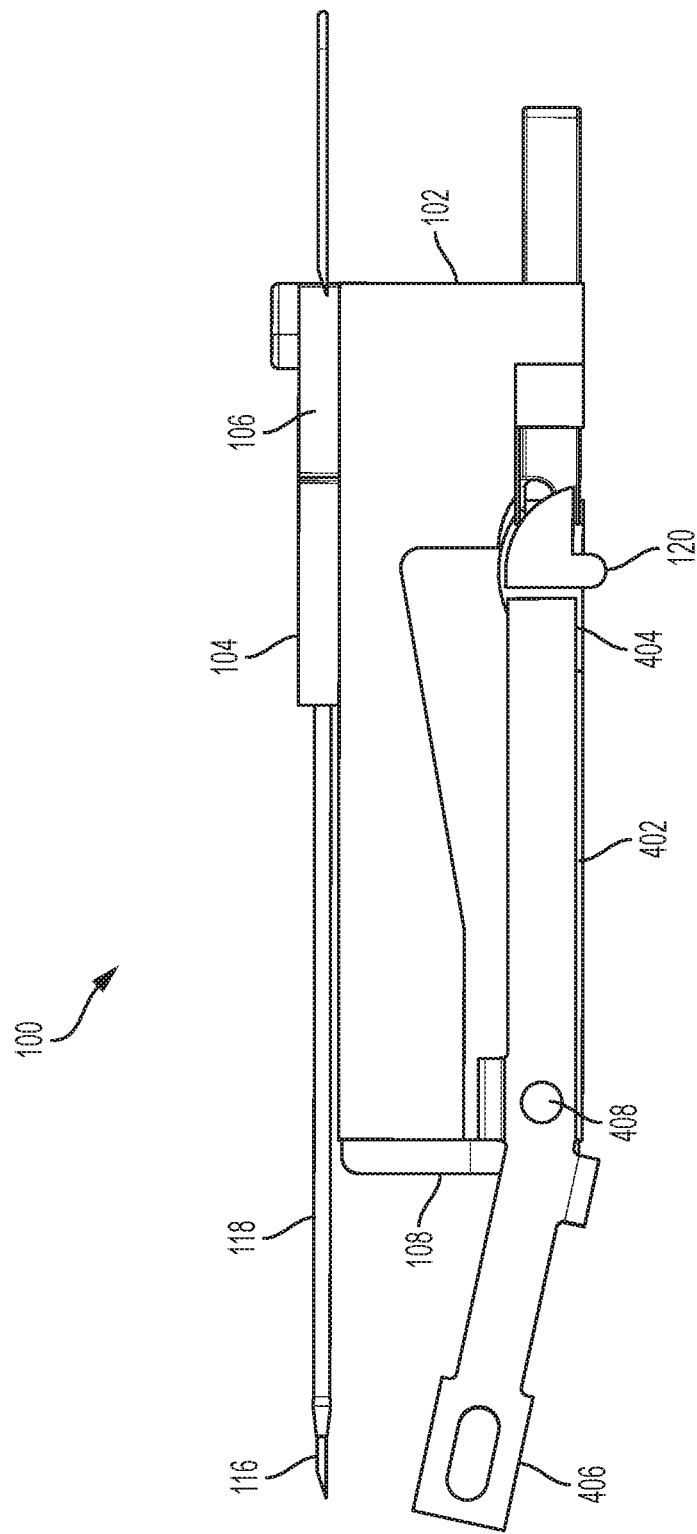
FIG. 4 illustrates a first side view of the needle mechanism module depicted in FIG. 1.

FIG. 4 illustrates a first side view of the needle mechanism module 100. FIG. 4 illustrates a needle mechanism module lock 402 relative to the lock 120 (the lock 120 can be considered to be a needle mechanism module insert lock). A first end 404 of the needle mechanism module lock 402 can be coupled to or positioned against or adjacent to the lock 120. The needle mechanism module lock 402 can prevent the lock 120 from moving. Consequently, the needle mechanism module lock 402 and the lock 120 can prevent the release of the slide insert 104 such that the slide insert 104 and the coupled slide retract 106 are prevented from moving toward the hard stop 108.

A second end 406 of the needle mechanism module lock 402 can be engaged to move the needle mechanism module lock 402. In various embodiments, the needle mechanism module lock 402 can rotate or pivot about a pivot point 408 when the second end 406 is pushed in a downward direction (e.g., relative to the needle mechanism module 100 depicted in FIG. 4). The second end 406 of the needle mechanism module lock 402 can be pushed in a downward direction by a purely mechanical mechanism or an electromechanical mechanism. In various embodiments, a user of the drug delivery device can press a button to activate the drug delivery device with the second end 406 being pushed down in response thereto (e.g., the second end 406 can be coupled to the button). In turn, the first end 404 can move upward in response by pivoting about the point 408 as described further herein.

In various embodiments, a user of the drug delivery device and/or the needle mechanism module 100 can engage a user interface component to initiate activation of the needle mechanism module 100. The user interface component can be any type of component or mechanism for initiating an action based on user input including a button, a slide, a touchscreen, a dial, a knob, or a switch.

Figure 5:
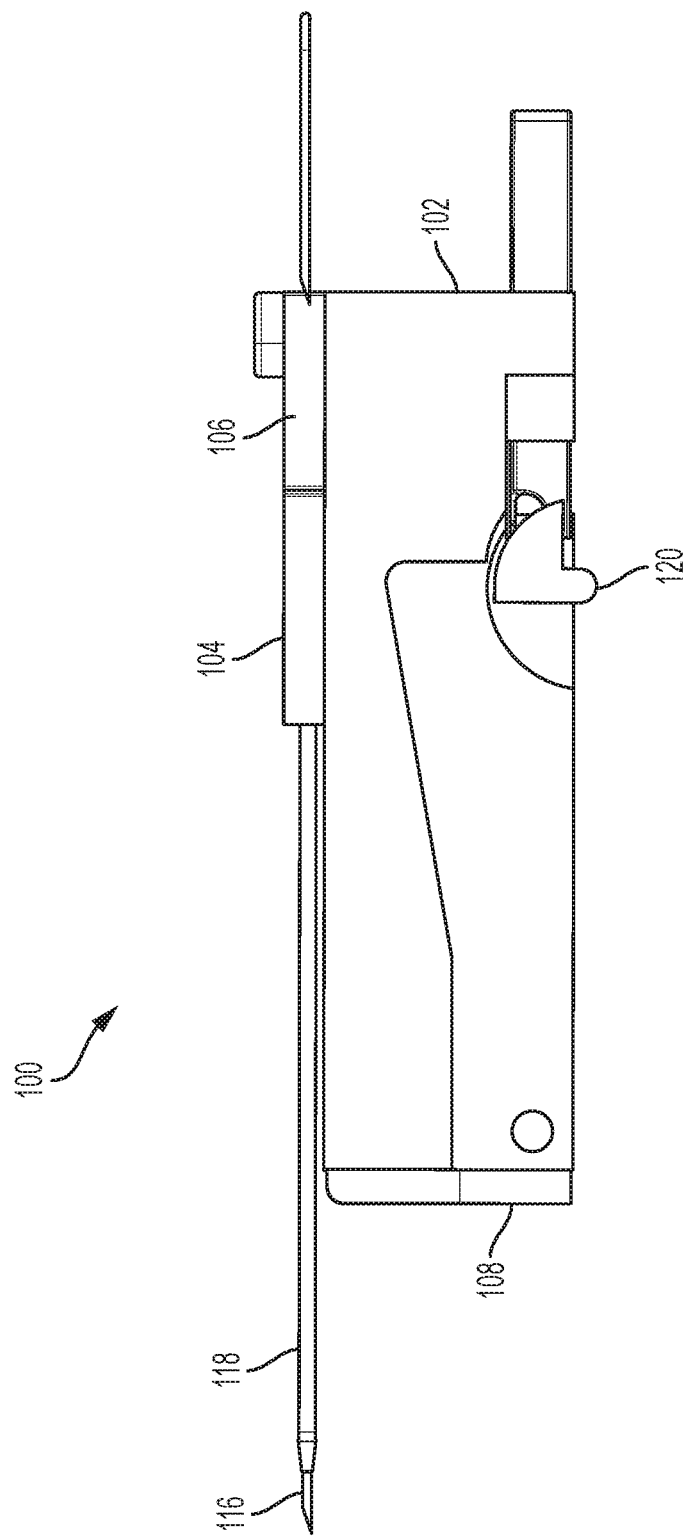
FIG. 5 illustrates a second side view of the needle mechanism module depicted in FIG. 1.

FIG. 5 illustrates the side view of the of the needle mechanism module 100 as depicted in FIG. 4 without the needle mechanism module lock 402 to further show the arrangement of the constituent components of the needle mechanism module 100. FIG. 5 shows the arrangement of the lock 102 relative to the rail 102 and the slide insert 104. FIGS. 1-5 depict the needle mechanism module 100 in an initial or pre-activation state. As can be seen, the needle 116 extends beyond the cannula 118 at an end of the needle mechanism module 100 near the hard stop 108. Further, the slide insert 104 and the slide retract 106 are positioned at the opposite end of the rail component 102.

Figure 6:
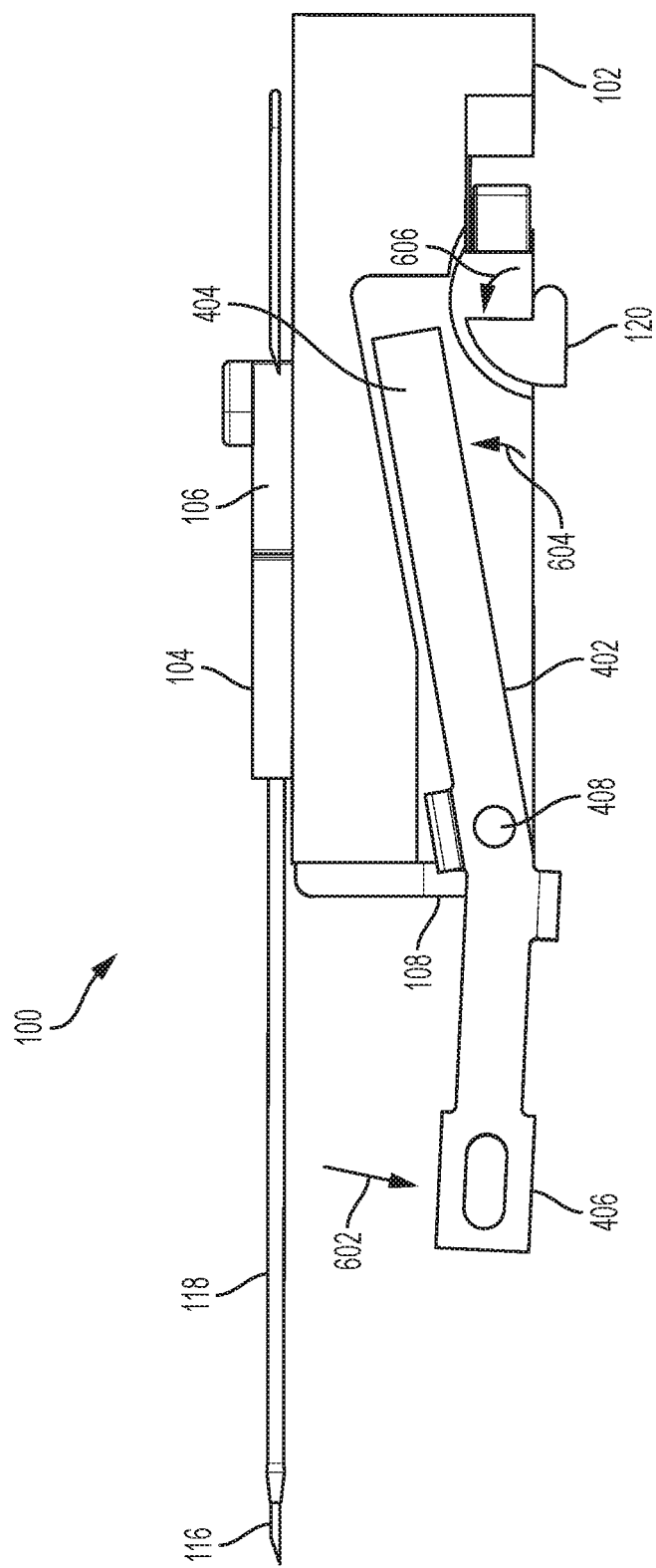
FIG. 6 illustrates a third side view of the needle mechanism module depicted in FIG. 1.

FIG. 6 illustrates release of the lock 120. FIG. 6 illustrates engagement of the of the needle mechanism module lock 402 relative to the side view of the needle mechanism module 100 as depicted in FIG. 4. As shown in FIG. 6, indicator 602 represents a downward movement of the second end 406 of the needle mechanism module lock 402. The second end 406 of the needle mechanism module lock 402 can be moved downward, for example, in response to the user pressing a button to activate the drug delivery device and/or the needle mechanism module 100. In response to the downward movement 602 of the second end 406 of the needle mechanism module lock 402, the first end 404 of the needle mechanism module lock 402 rotates upward about pivot 408. Indicator 604 illustrates a movement of the first end 404 of the needle mechanism module lock 402 in response to the downward movement 602 of the first end 404.

Movement of the needle mechanism module lock 402 as shown in FIG. 6 decouples the needle mechanism module lock 402 from the lock 120. In particular, the first end 404 of the needle mechanism module lock 402 is no longer adjacent to or positioned against the lock 120. As a result, the first end 404 of the needle mechanism module lock 402 no longer restricts movement of the lock 120. Accordingly, the lock 120 can be allowed to move. In various embodiments, the lock 120 can rotate (e.g., rotate counter-clockwise) as shown by indicator 606. This movement—as represented by indicator 606—can represent releasing the lock 120.

After movement of the lock 120, the slide insert 104 (and the coupled slide retract 106) can be free to move—for example, toward the hard stop 108 as described further herein and as shown in FIG. 6. FIG. 6 can represent the needle mechanism module 100 during initial activation—e.g., when a user first engages a button to fire or activate the needle mechanism module 100 and the slide insert 104 and the slide retract 106 first move toward the hard stop 108. For example, as shown in FIG. 6, the slide insert 104 and the slide retract 106 have advanced toward the hard stop 108 from the opposite end of the rail 102.

Figure 7:
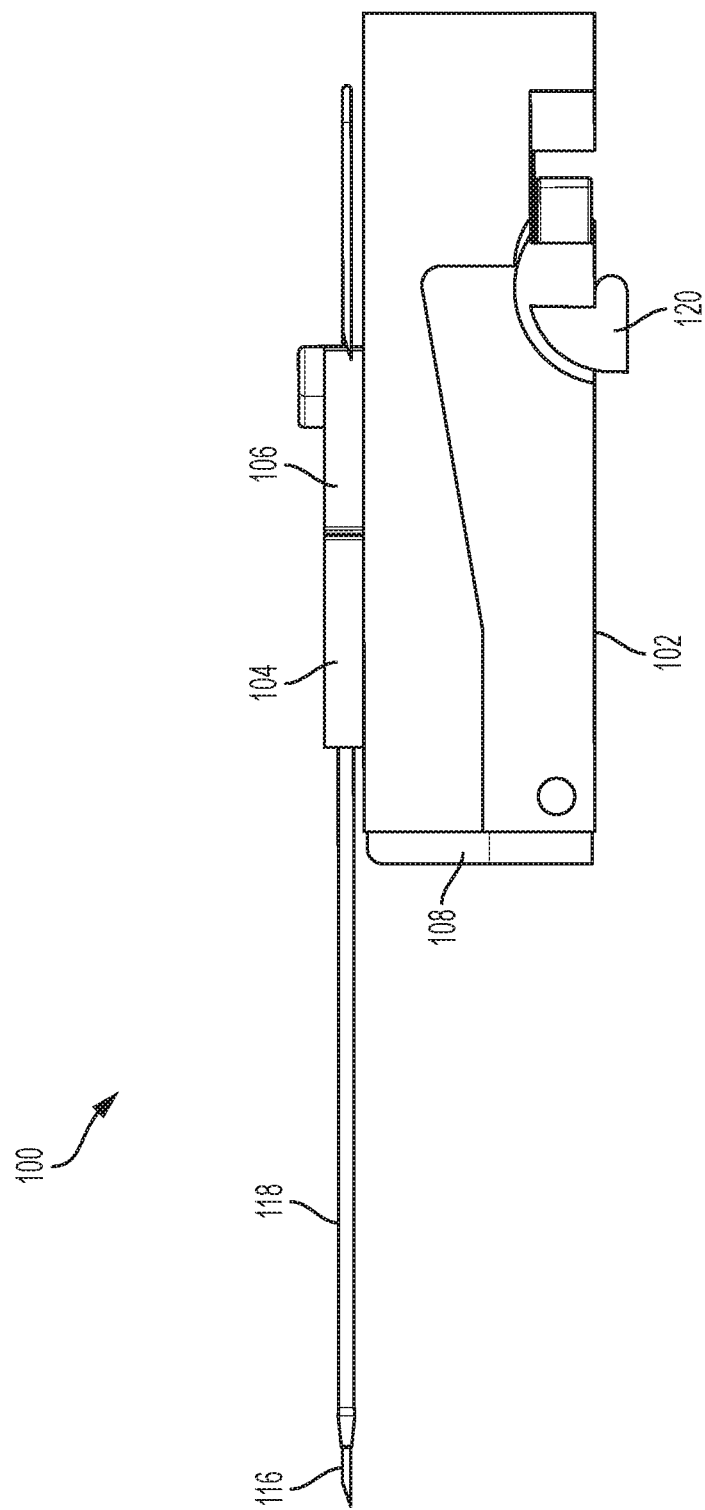
FIG. 7 illustrates a fourth side view of the needle mechanism module depicted in FIG. 1.

FIG. 7 illustrates the side view of the of the needle mechanism module 100 as depicted in FIG. 6 without the needle mechanism module lock 402 to further show the arrangement of the constituent components of the needle mechanism module 100. FIG. 7 shows the lock 120 as moved or rotated (e.g., in an unlocked or released position or state) after restriction of the movement of the lock 120 has been removed and relative to the initial position or state of the lock as depicted in, for example, FIG. 5. FIGS. 6 and 7 illustrate the needle mechanism module 100 during activation—e.g., when the lock 120 is released to enable movement of the slide insert 104 and the slide retract 106 toward the hard stop 108.

Figure 8:
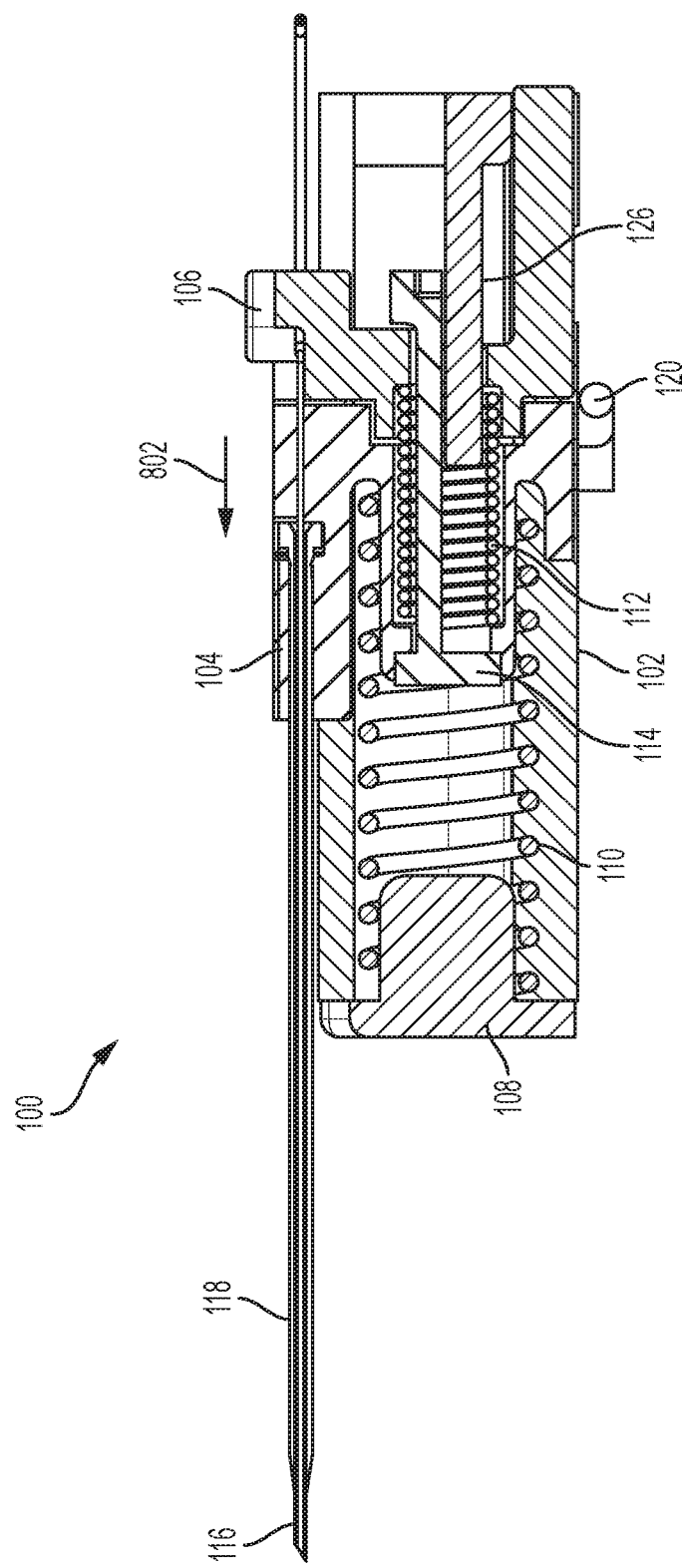
FIG. 8 illustrates a second cross-sectional side view of the needle mechanism module during insertion of a needle and a cannula.

FIG. 8 illustrates further activation of the needle mechanism module 100. In particular, FIG. 8 shows the needle mechanism module 100 as the slide insert 104 and the slide retract 106 as a coupled unit initial moves toward the hard stop 108 by action of the insertion spring 110. Indicator 802 shows a direction of movement of the slide insert 104 and the slide retract 106 relative to their initial positions. Indicator 802 also shows the direction of movement of the needle 116 an the cannula 118.

As shown in FIG. 8, the slide insert 104 and the slide retract 106 are positioned closer to the hard stop 108 relative to the positioning of the slide insert 104 and the slide react 106 as shown in FIG. 1. The coils of the insert spring 110 are shown to be closer together as the insert spring 108 exerts a force to draw the slide insert 104 to the hard stop 108. The needle 116 and the cannula 118 move with the slide insert 104. As a result, the needle 116 can be moved toward the user and can be inserted into the patient. FIG. 8 can represent a partial insertion of the needle 116 and can also represent partial insertion of the cannula 118.

The slide insert 104 and the slide retract 106 can continue moving in the direction 802 until the slide insert 104 meets the hard stop 108. In particular, the slide insert 104 can continue moving in the direction 802 until the end of the tension lock component 114 is positioned adjacent to the hard stop 108. During the movement of the slide insert 104 toward the hard stop 108, a portion of the needle 116 can be further inserted into the patient (along with a portion of the cannula 118). FIG. 8 shows a cross-sectional side view of the needle mechanism module 100.

Figure 9:
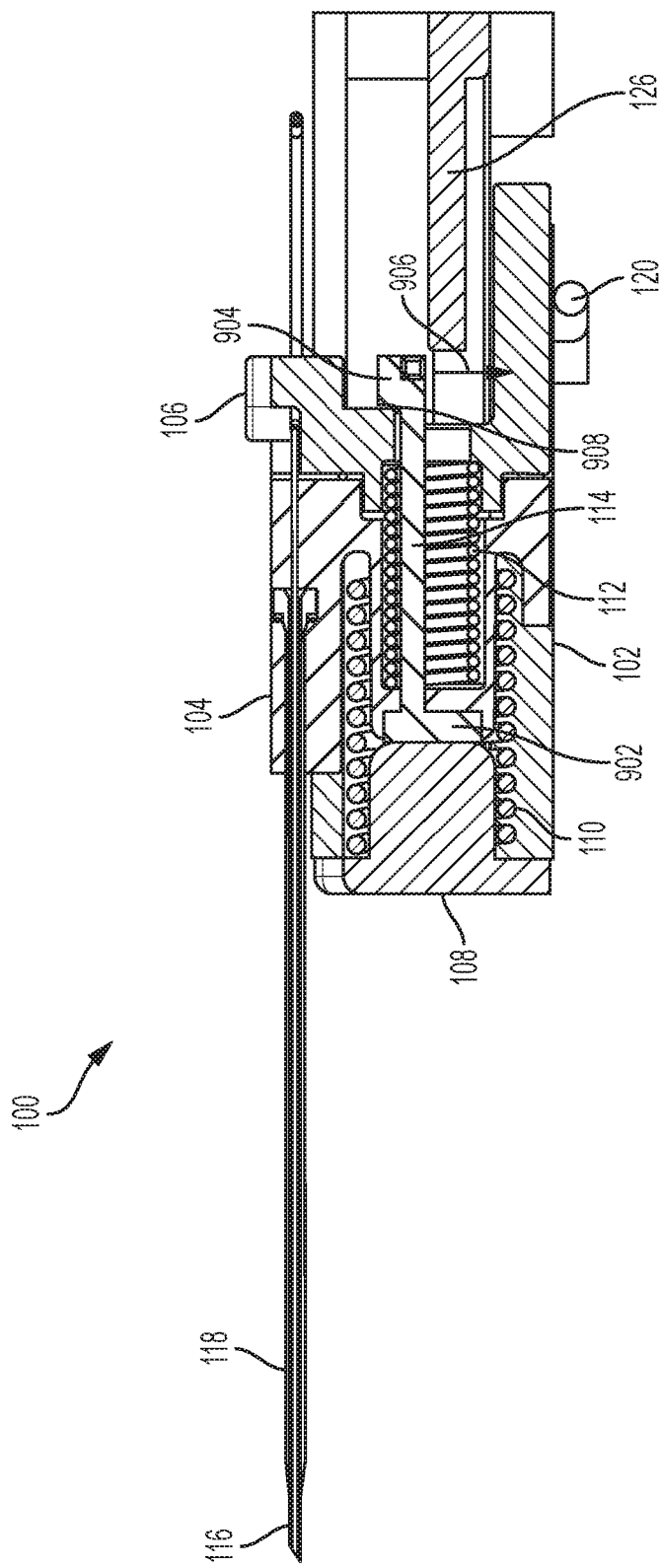
FIG. 9 illustrates a third cross-sectional side view of the needle mechanism module during insertion of the needle and the cannula.

FIG. 9 illustrates the needle mechanism module 100 with the needle 116 fully inserted into the patient (e.g., inserted to a maximum depth or by a maximum amount). As shown in FIG. 9, a front portion or first end 902 of the tension lock 114 is positioned against the hard stop 108. Accordingly, the hard stop 108 prevents any further movement of the slide insert 104 when the first end 902 is so positioned. The movement of the slide insert 104 from its initial position (e.g., as shown in FIG. 1) to the position where the tension lock 114 is positioned against the hard stop 108 (e.g., as shown in FIG. 9) can determine the fully inserted position of the needle 116. FIG. 9 also illustrates a cross-sectional side view of the needle mechanism module 100.

When the tension lock 114 is positioned against the hard stop 108 as shown in FIG. 9, a second end or back portion 904 of the tension lock 114 can extend beyond the rail beam 126. When the back portion 904 of the tension lock 114 extends beyond the beam 126, the tension lock 114 is able to deflect downwards as shown by indicator 906. Further, the slide retract 106 can include an angled portion 908 in proximity to the interface of the slide retract 106 and the tension lock 114. The angled portion 908 at this interface can cause or help the tension lock 114 to be pushed or deflected downward based on a force provide by the retract spring 112.

In particular, the retract spring 112 can be biased to push the side insert 104 and the slide retract 106 apart but can be prevented from doing so while the tension lock component 114 is positioned over and/or adjacent to the rail beam 126. When the tension lock component 114 moves far enough toward the hard stop 108 to no longer be positioned over the rail beam 126, the tension lock component 114 may no longer function to keep the slide insert 104 and the slide retract 106 coupled together as described herein. FIG. 9 can represent the needle mechanism module 100 when the needle 116 is fully inserted into the patient and just prior to retraction of the needle 116.

Figure 10:
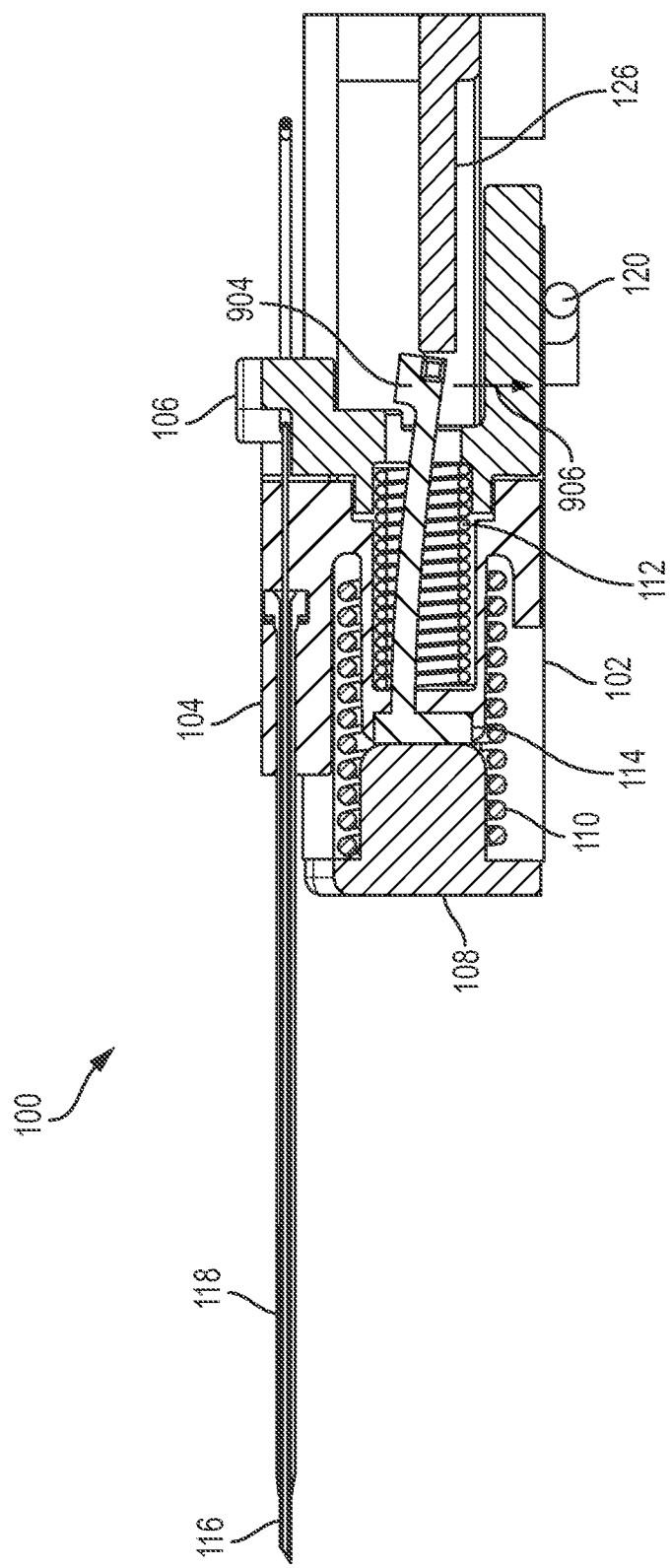
FIG. 10 illustrates a fourth cross-sectional side view of the needle mechanism module during retraction of the needle.

FIG. 10 illustrates the needle mechanism module 100 during an initial stage of retraction of the needle 116. As shown in FIG. 10, the tension lock 114 is deflected downward (e.g., relative to the position of the tension lock 114 as shown in FIG. 9). Prior to being deflected downward, the tension lock 114 retains the slide retract 106 against the slide insert 104. When the back portion 904 of the tension lock 114 is no longer over top of the rail beam 126, the rail beam 126 no longer restricts the downward movement of the tension lock 114. When the tension lock 114 moves downward, the slide retract 106 is capable of being removed from or decoupled from the slide insert 104 by a movement or force of the retract spring 112. In various embodiments, the spring 112 can begin to expand to force the tension lock portion 904 downward as the spring 112 begins to push the slide retract away from the hard stop 108 and the slide insert 104. FIG. 10 illustrates the needle mechanism module 100 just prior to the slide retract 106 moving away from the slide insert 104 (e.g., in a direction away from the hard stop 108). Further, FIG. 10 can represent an operation state of the needle mechanism module 100 with the cannula 118 inserted into the patient or user.

Figure 11:
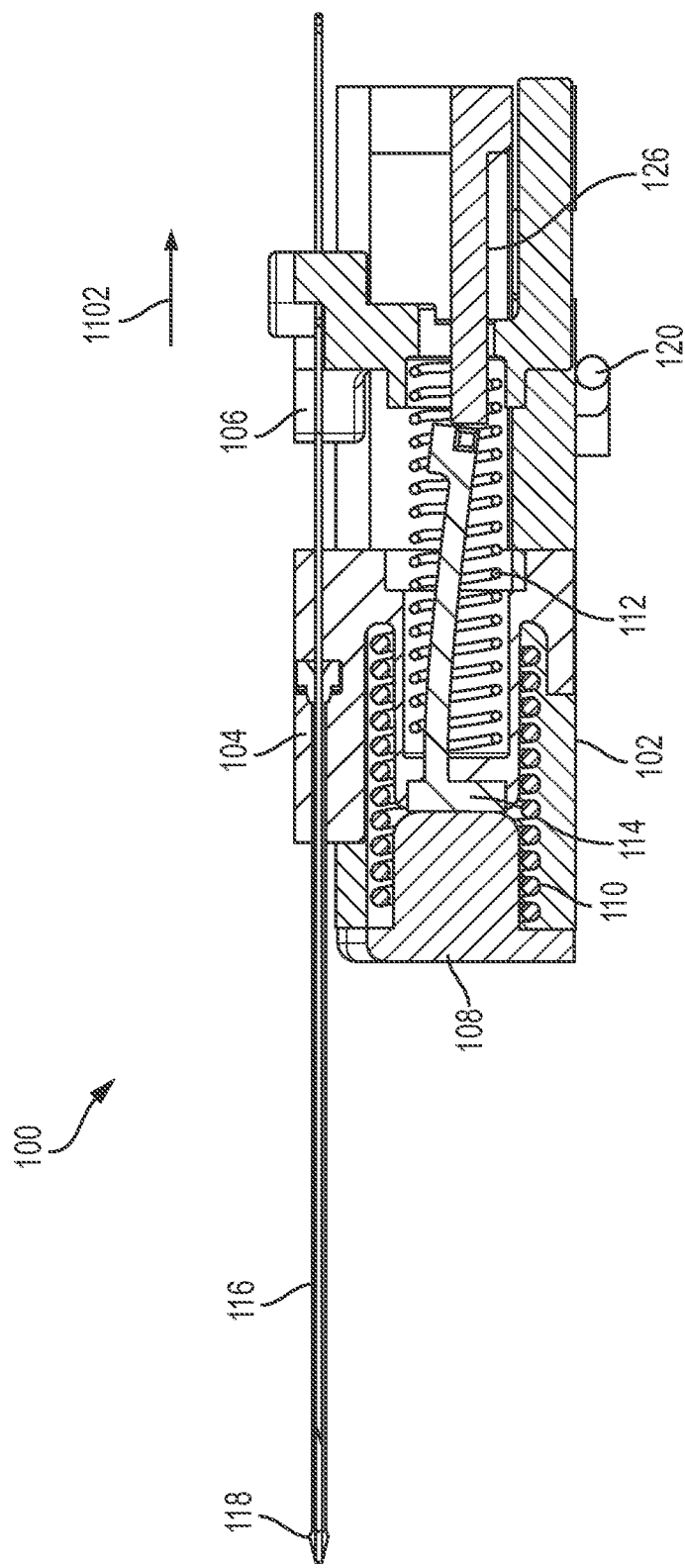
FIG. 11 illustrates a fifth cross-sectional side view of the needle mechanism module during retraction of the needle.

FIG. 11 illustrates the needle mechanism module 100 during retraction. Specifically, FIG. 11 illustrates the needle mechanism module 100 during a partially retracted state of the needle 116 relative to the position of the needle 116 as shown in FIG. 9. As shown in FIG. 11, the slide retract 106 is moving away from the needle insert 104 in a direction 1102. The expansion of the retract spring 112 can cause the slide retract 106 to move in the direction 1102 relative to the stationary slide insert 104 which remains positioned against the hard stop 108. As shown in FIG. 11, the needle 116 is retracted inside of the cannula 118 (e.g., as it moves in the direction 1102 with the slide retract 106) while the cannula 118 remains stationary (and coupled to the slide insert 104). As a result of the movement of the slide retract 106 and the needle 116 coupled thereto, the needle 116 can be removed from the patient and the cannula 118 can remain inside of the patient, maintaining the fluid path component from the stored liquid drug to the patient. The slide retract 106 can continue moving in the direction 1102 until the retract spring 112 is expanded further.

Figure 12:
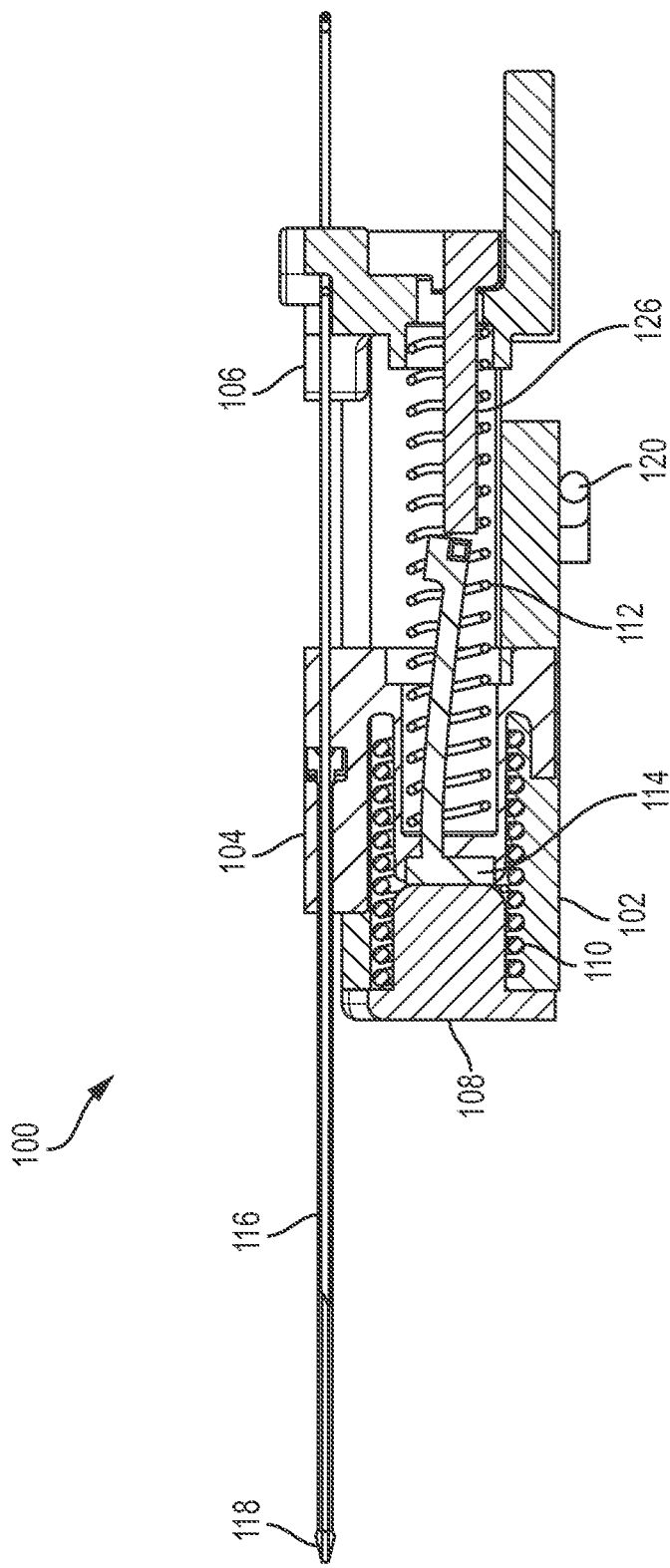
FIG. 12 illustrates a sixth cross-sectional side view of the needle mechanism module after retraction of the needle.

FIG. 12 illustrates the needle mechanism module 100 when the needle 116 is fully retracted. As shown in FIG. 12, the retraction spring 110 is more fully expanded. The slide retract 106 is positioned at its furthest distance away from the slide insert 104. For example, the slide retract 106 can be positioned at a far end of the rail 102 opposite the end of the rail 102 coupled to the hard stop 108. The needle 116 has retracted further inside of the cannula 118 relative to the position of the needle 116 as depicted in FIG. 11. Meanwhile, the cannula 118 remains stationary and can be left inserted into the patient.

FIG. 12 can represent the needle mechanism module 100 after completion of the retraction of the needle 116. The stored liquid drug can be provided to the patient by the fluid path component that can include the needle 116 and the cannula 118. A portion of the end of the cannula 118 that extends beyond the end of the needle 116 can be positioned within the patient.

Figure 13:
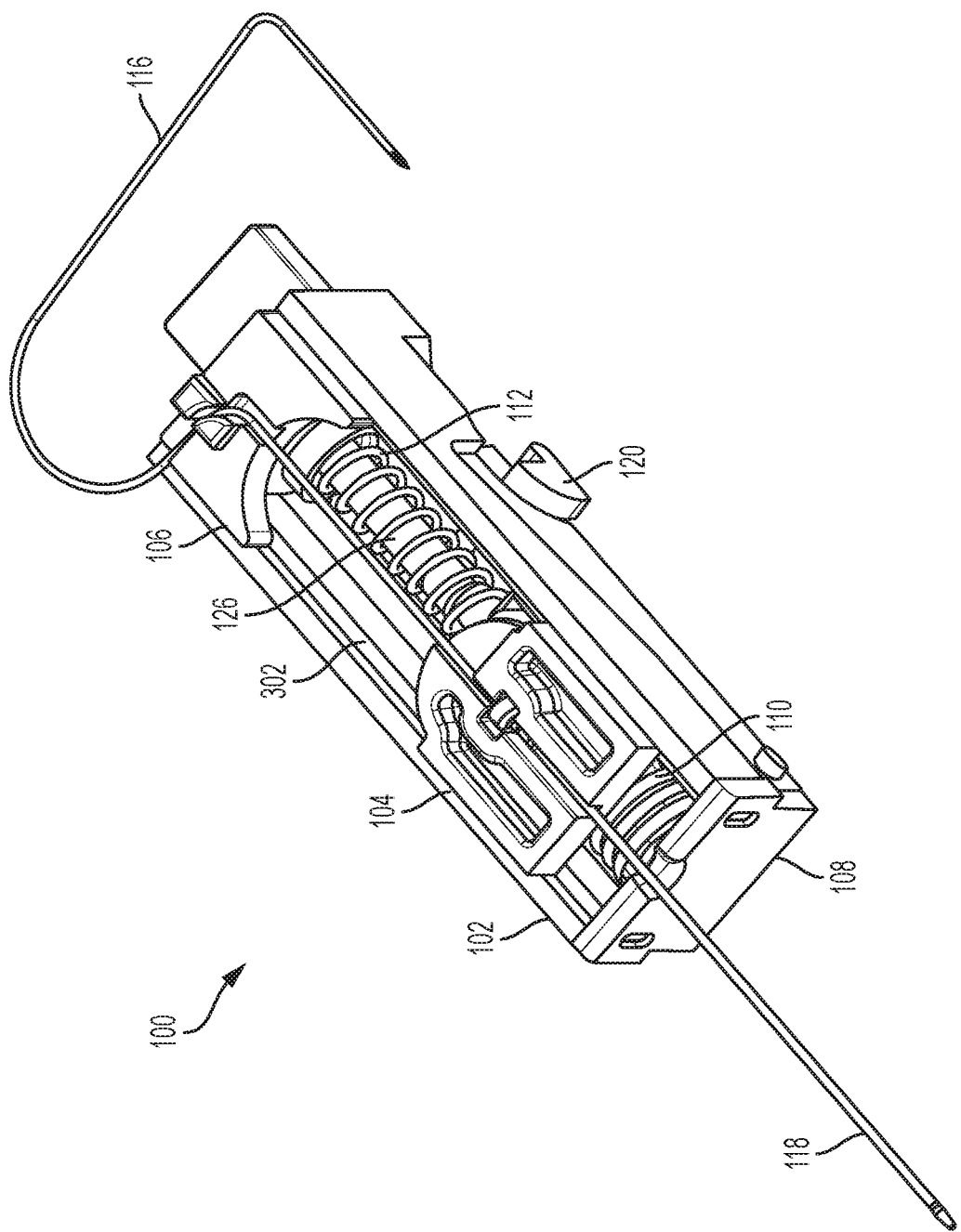
FIG. 13 illustrates an overhead side view of the needle mechanism module depicted in FIG. 12.

FIG. 13 illustrates an overhead side view of the needle mechanism module 100 as depicted in FIG. 12. FIG. 13 illustrates the arrangement and positioning of the needle insert 104 and the needle retract 106 after retraction of the needle 116 is completed. As shown in FIG. 13, a complete fluid path is provided to the patient through coupling of the needle 116 to a stored liquid drug, the coupling of the needle 116 to the cannula 118, and the coupling the cannula 118 to the patient. The slide insert 104 is positioned against the hard stop 108 at a first end of the rail 102. The slide retract 106 is positioned at an opposite end of the rail 102. The retract spring 112 can maintain the separation of the slide insert 104 and the slide retract 106 as shown in FIG. 13.

Figure 14:
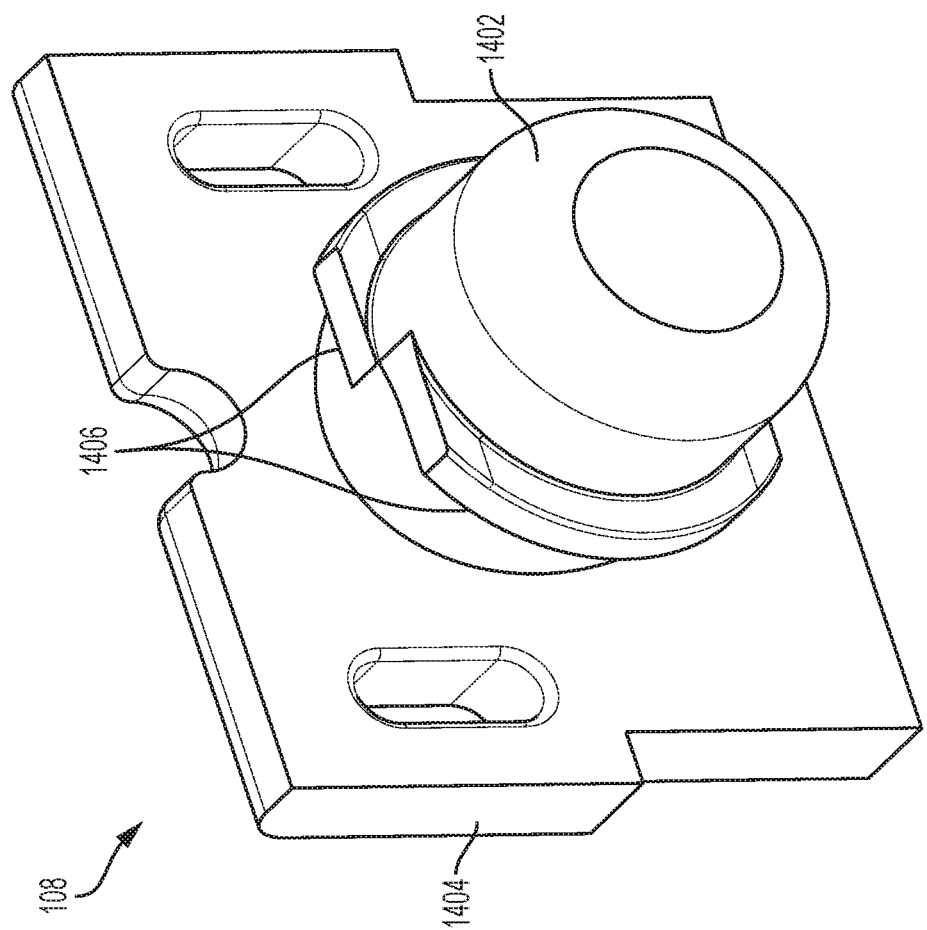
FIG. 14 illustrates a first component of the needle mechanism module.

FIG. 14 illustrates a close-up view of the hard stop 108. As shown in FIG. 14, the hard stop 108 can include a first portion 1402 and a second portion 1404. The first portion 1402 can extend from the second portion 1404. The second portion 1404 can be a base portion. The first portion 1402 can be a cylindrically-shaped portion that extends from the second portion 1404. As further shown in FIG. 14, the first portion 1402 can include one or more components 1406 positioned along the first portion 1402. The components 1406 can extend radially from the first portion 1402. The components 1406 can be used to hold or retain an end of the insert spring 110. The base portion 1404 can be coupled to an end of the rail 102. The first portion 1402 can extend into the open area of the rail 102.

Figure 15:
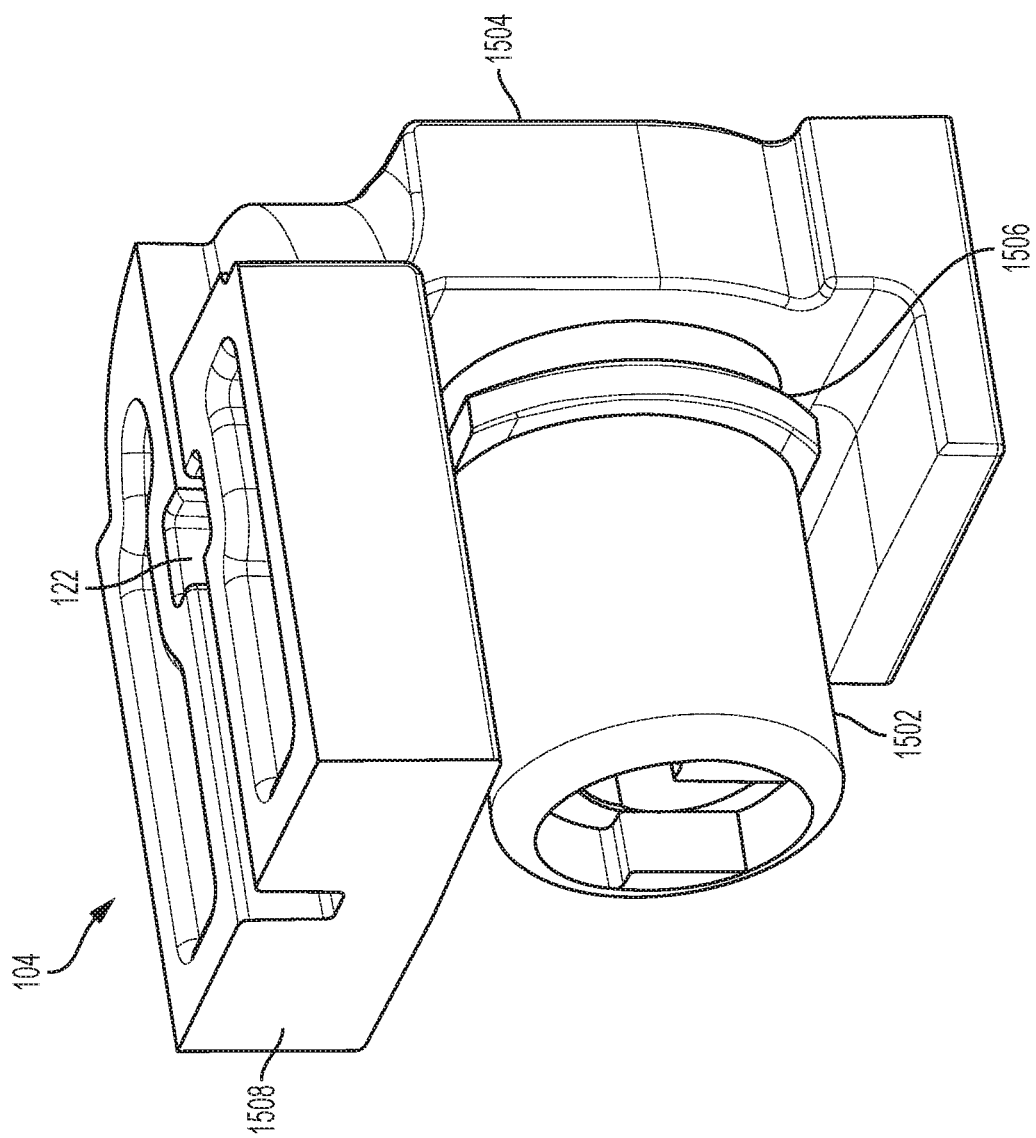
FIG. 15 illustrates a second component of the needle mechanism module.

FIG. 15 illustrates a close-up view of the slide insert 104. As shown in FIG. 15, the slide insert 104 can include a first portion 1502 and a second portion 1504. The first portion 1502 can extend from the second portion 1504. The second portion 1504 can be a base portion. The first portion 1502 can be a cylindrically-shaped portion that extends from the second portion 1504. As further shown in FIG. 15, the first portion 1502 can include one or more components 1506 positioned along the first portion 1502. The components 1506 can extend radially from the first portion 1502. The components 1506 can be used to hold or retain an end of the insert spring 110 (e.g., an end opposite the end of the insert spring 110 that is held in place by the components 1406 depicted in FIG. 14).

The slide insert 104 can further include a top portion 1508. The pocket or opening 122 can be positioned on a top side of the top portion 1508. An underside of the top portion 1508 can rest and move along the rails 302 of the rail base component 102. The pocket 122 can include a channel or opening allowing the needle 116 and cannula 118 to be positioned within it for stability.

Figure 16:
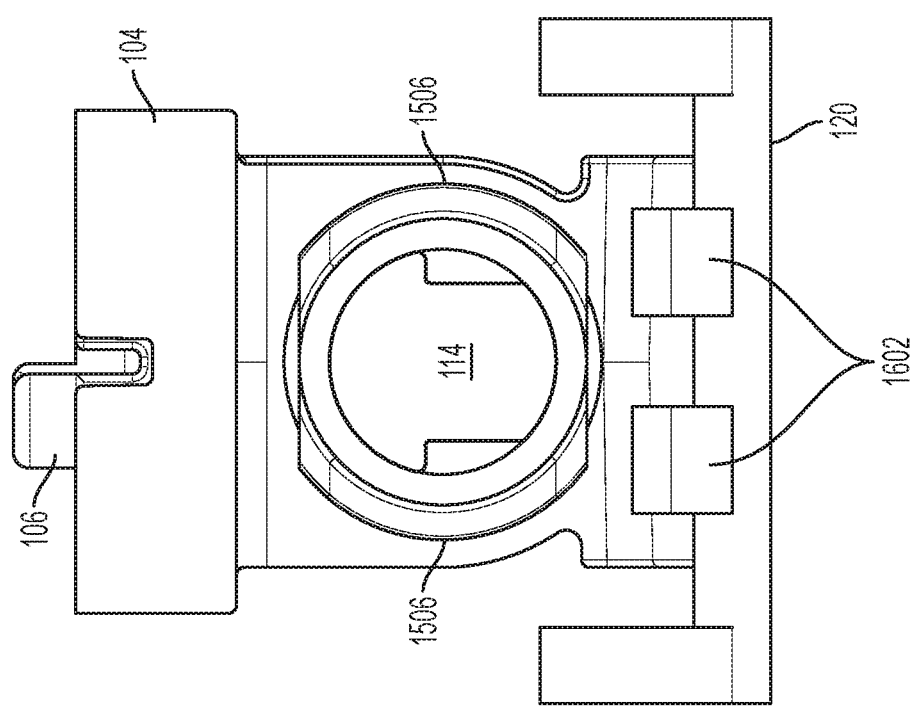
FIG. 16 illustrates a front view of various components of the needle insertion mechanism.
Figure 17:
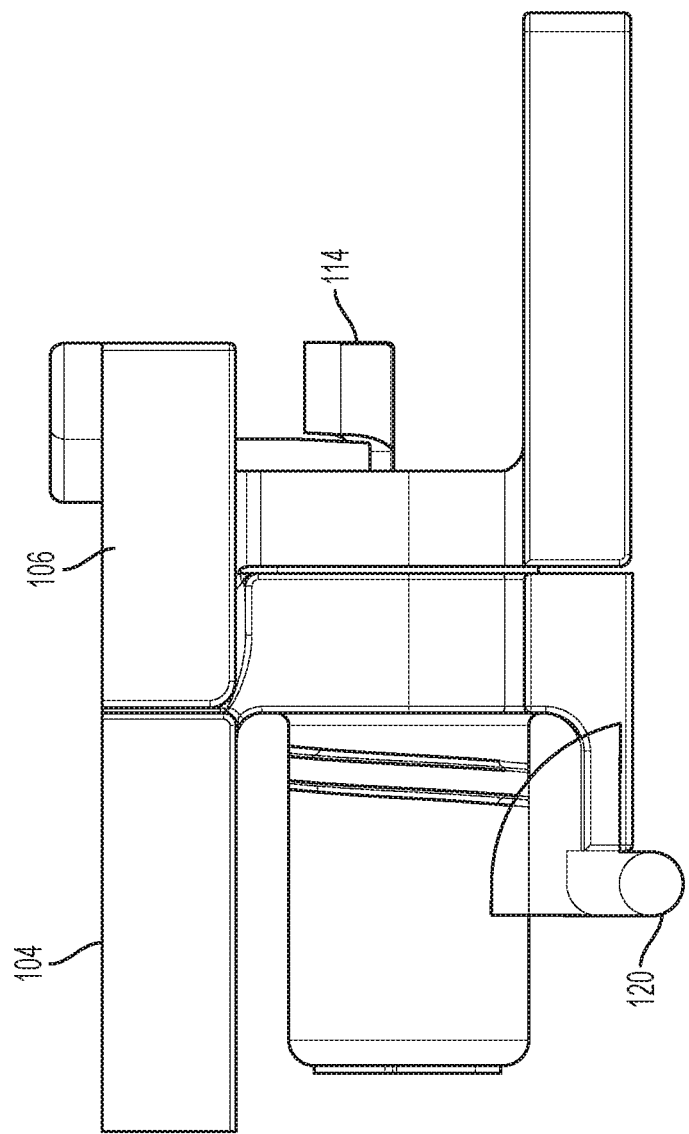
FIG. 17 illustrates a side view of the various components of the needle insertion mechanism depicted in FIG. 16.
Figure 18:
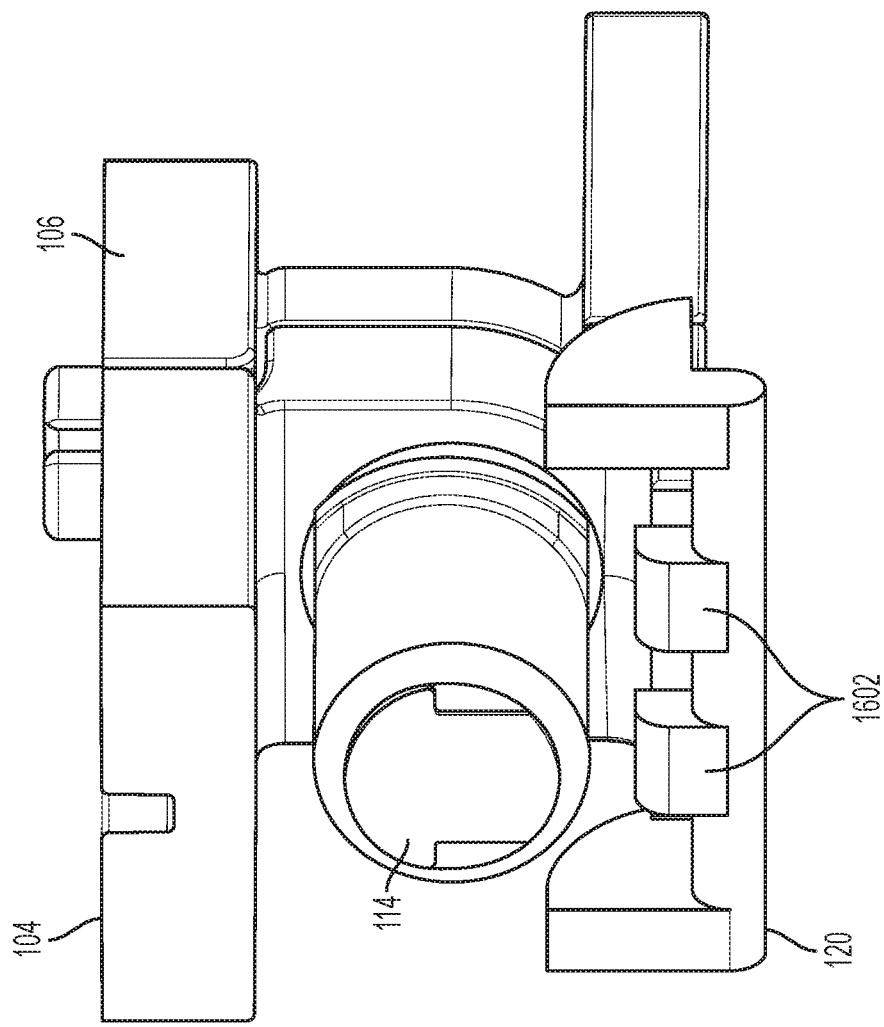
FIG. 18 illustrates an angled view of the various components of the needle insertion mechanism depicted in FIG. 16.

FIGS. 16-18 shows various views of the arrangement of the slide insert 104 and the slide retract 106 relative to the lock 120. FIG. 16 shows a front view of the slide insert 104, slide retract 106, and the lock 120. FIG. 17 shows a side view of the slide insert 104, slide retract 106, and the lock 120. FIG. 18 shows a view of the of the slide insert 104, slide retract 106, and the lock 120 at an angle—e.g., an angle between the views shown in FIGS. 16 and 17. FIGS. 16-18 show the lock 120 in an initial locked position.

As shown in FIGS. 16-18, the lock 120 can include interior raised components 1602. The components 1602 can restrict movement of the slide insert 104. Prior to the lock 102 being rotated as described above, the components 1602 can be positioned against a portion of the slide insert 104 and can restrict the movement of the slide insert 104. Once the lock 120 is rotated, the components 1602 can be moved away from and out of contact with the slide insert 104. As a result, the slide insert 104 is no longer restricted from moving, enabling the needle 116 of the needle mechanism module 100 to be inserted as described above.

Figure 19:
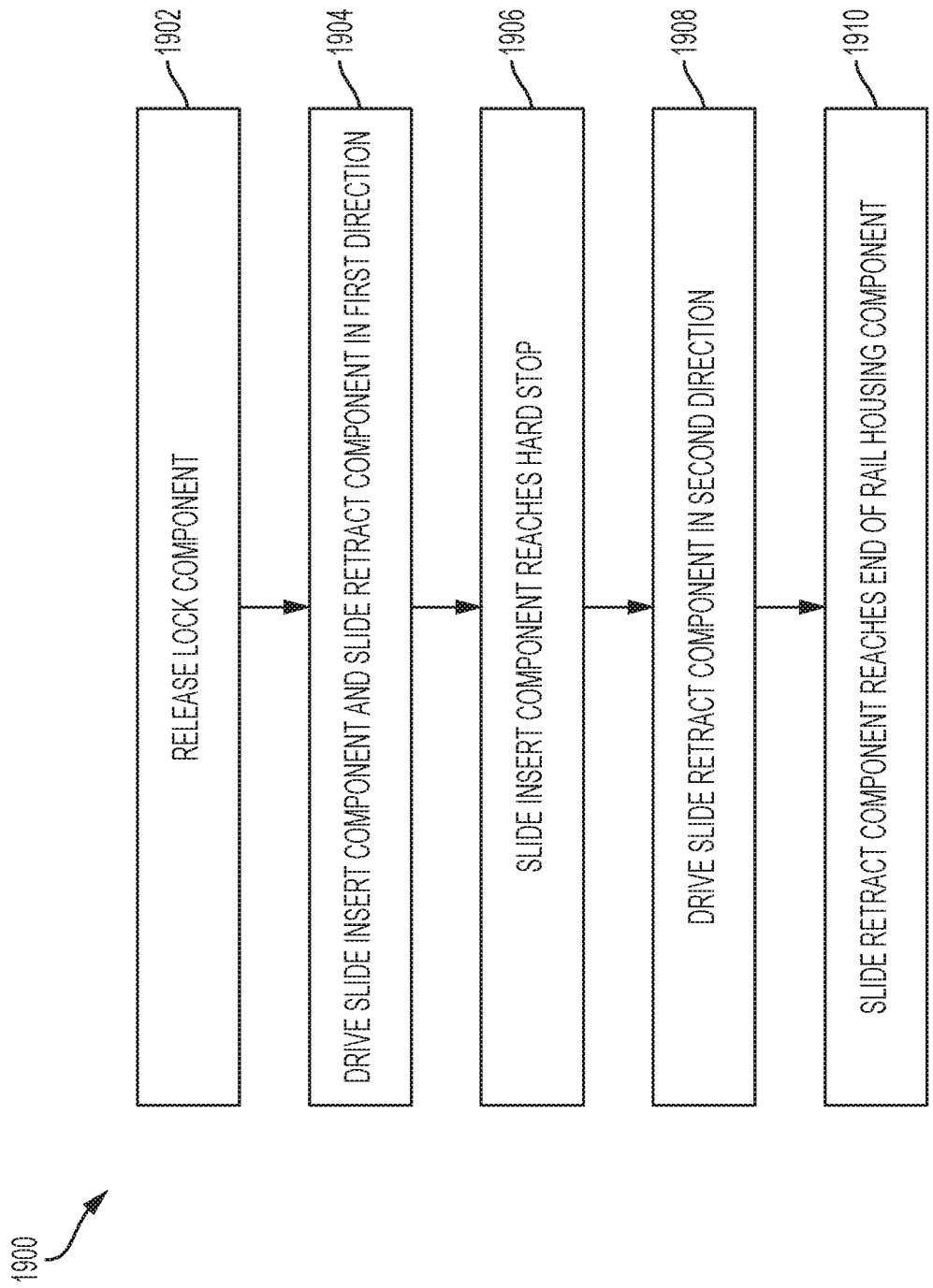
FIG. 19 illustrates a method of operation for the needle mechanism module depicted in FIG. 1.

FIG. 19 illustrates an exemplary method of operation 1900 for inserting a needle into a patient and then retracting the needle from the patient while maintaining a cannula coupled to the patient. The method of operation 1900 can be implemented by the needle mechanism module 100.

At 1902, a lock 120 of the needle mechanism module 100 can be released. The lock 120 can be released in any number of manners. In various embodiments, the lock 120 can be released by engaging a needle mechanism module lock 402. The needle mechanism module lock 402 can be engaged directly by a user or indirectly by a user. For example, the mechanism module lock 402 can respond to mechanical or electrical engagement by a user pressing a button. Releasing the lock 120 can no longer restrict movement of a slide insert 104 and a slide retract 106.

At 1904, the slide insert 104 and the slide retract 106 can be driven toward the patient. A spring 110 coupled to a hard stop 108 and coupled to the slide insert 104 can be biased to bring the slide insert 104 toward the hard stop 108 once the lock 102 is released. The slide retract 106 can be coupled to the slide insert 104 so as to move toward the hard stop 108 when the lock 102 is released. The hard stop 108 can be attached to a far end of a rail housing component 102, opposite an end from which the slide insert 104 and the slide retract 106 are initially positioned.

A needle 116 and a cannula 118 can be coupled to the slide insert 104 and can both be advanced toward the patient as the slide insert 104 is advanced toward the hard stop 108. The movement of the needle 116 and the cannula 118 toward the patient can eventually cause the needle 116 to pierce the patient, allowing the needle 116 and/or the cannula 118 to enter the patient.

At 1906, the slide insert 104 can reach the hard stop 108. When the slide insert 104 reaches the hard stop 108, the needle 116 and the cannula 118 are prevented from further entering the patient. Accordingly, a maximum insertion depth of the needle 116 and/or the cannula 118 can be reached. Further, when the slide insert 104 reaches the hard stop 108, a tension lock component 114 can extend beyond a rail beam 126. The tension lock component 114 can maintain a coupling or attachment between the slide insert 104 and the slide retract 106 as long as the rail beam 126 is positioned adjacent to the tension lock component 114. The rail beam 126 can be stationary while the tension lock component 114 can be coupled to the slide insert 104 and the slide retract 106. Accordingly, as the slide insert 104 and the slide retract 106 move toward the hard stop 108, the tension lock component 114 moves along the rail beam 126. Eventually, when the slide inset 104 reaches the hard stop 108, the tension lock component 114 can move beyond the rail beam 126, such that the tension lock component 114 and the rail beam component 126 are no longer overlapping or adjacent to one another.

At 1908, since the tension lock component 114 no longer overlaps the stationary rail beam 126, the tension lock component 114 can be bent downward in response to expansion of a spring 112. The spring 112 can be coupled between the slide insert 104 and the slide retract 106. The spring 112 can be prevented from expanding when the tension lock component 114 is not able to be bent or deflected downwards, thereby ensuring the slide insert 104 and the slide retract 106 are maintained in close proximity or coupled closely together. Once the tension lock component 114 clears the rail beam 126 and is free to be deflected downwards, the spring 112 can expand. As the spring 112 expands, the spring 112 can force the slide retract 106 to move away from the slide insert 104. In particular, the slide insert 104 can remain stationary and pressed against the hard stop 108 as the slide retract moves back toward the opposite end of the rail housing component 102.

The movement of the slide retract 106 away from the hard stop 108 can retract the needle 116. The needle 116 can be retracted out of the patient. The cannula 118 can remain coupled inside of the patient as it is coupled to the slide insert 104. Accordingly, at 1908, the needle 116 can be retracted from the patient without disturbing the positioning of the cannula 118 which is inserted into the patient at 1906.

At 1910, the slide retract 106 can reach the far end of the rail housing component 102. The needle 116 can be fully retracted from the user while the slide insert 104 and the cannula 118 remain stationary, with the cannula 118 remaining inserted into the user.

The following examples pertain to further embodiments:

Example 1 is a needle mechanism module comprising a rail housing component, a slide insert component coupled to the rail housing component and configured to slide along the rail housing component, a slide retract component coupled to the rail housing component and configured to slide along the rail housing component, a hard stop component coupled to a first end of the rail housing component, the slide insert component and the slide retract component positioned toward a second, opposite end of the rail housing component, the slide insert component positioned closer to the hard stop component, an insert extension spring coupled to the hard stop component and to the slide insert component, a retract compression spring positioned between the slide insert component and the slide retract component, a tension lock component positioned through the slide insert component and the slide retract component and configured to couple the slide insert component to the slide retract component, an insert lock positioned against the slide insert component and configured to restrict movement of the slide insert component and the slide retract component toward the hard stop by the insert spring, a needle coupled to the slide insert component and the slide retract component, the needle further coupled to a liquid drug stored in a reservoir of a wearable drug delivery device, and a cannula surrounding a portion of the needle extending from the slide insert component, an end of the cannula coupled to the slide insert component.

Example 2 is an extension of Example 1 or any other example disclosed herein, further comprising a needle mechanism module lock coupled to the insert lock, the needle mechanism module lock configured to restrict movement of the insert lock.

Example 3 is an extension of Example 2 or any other example disclosed herein, wherein the needle mechanism module lock is coupled to a push button.

Example 4 is an extension of Example 3 or any other example disclosed herein, wherein the needle mechanism module is configured to remain in an idle state until a user engages the push button.

Example 5 is an extension of Example 4 or any other example disclosed herein, wherein the needle mechanism module lock is configured to allow movement of the insert lock responsive to the user engaging the push button.

Example 6 is an extension of Example 5 or any other example disclosed herein, wherein the insert lock is configured to rotate when allowed to move and to allow movement of the slide insert component and the slide retract component.

Example 7 is an extension of Example 6 or any other example disclosed herein, wherein the slide insert component and the slide retract component are configured to move along the rail housing component toward the hard stop component when allowed to move based on a force provided by the insert extension spring.

Example 8 is an extension of Example 7 or any other example disclosed herein, wherein the needle and the cannula are configured to move with the slide insert component and the slide retract component and are configured to be inserted into the user as the slide insert component and the slide retract component move toward the hard stop component.

Example 9 is an extension of Example 8 or any other example disclosed herein, wherein when the tension lock component meets the hard stop component, an end of the tension lock component positioned furthest from the hard stop component is configured to deflect downward to enable the retract compression spring to expand, wherein prior to the tension lock component meeting the hard stop component, a rail beam of the rail housing component is configured to prevent the end of the tension lock component from deflecting downward.

Example 10 is an extension of Example 9 or any other example disclosed herein, wherein the needle is inserted into the user by a maximum amount when the tension lock component meets the hard stop component.

Example 11 is an extension of Example 10 or any other example disclosed herein, wherein the slide insert component and the cannula remain stationary and the slide retract component and the needle retract away from the hard stop component toward the second end of the rail housing component as the retract compression spring expands, thereby removing the needle from the user and leaving the cannula in the user.

Example 22 is a method comprising releasing a lock component, driving a slide insert component and a slide retract component in a first direction from a first end of a rail housing component to a second, opposite end of the rail housing component, inserting a needle and a cannula into a user as the slide insert component is driven toward the second end of the rail housing component, the needle and the cannula coupled to the slide insert component, deflecting a tension lock component downward to allow a retract compression spring positioned between the slide insert component and the slide retract component to expand, driving the slide retract component in a second, opposite direction from the second end of the rail toward the first end of the rail, and removing the needle from the user while the cannula remains inserted in the user.

Example 13 is an extension of Example 12 or any other example disclosed herein, further comprising restricting movement of the slide insert component and the slide retract component toward the second end of the rail housing component prior to releasing the lock component.

Example 14 is an extension of Example 13 or any other example disclosed herein, further comprising releasing the lock component in response to the user engaging a user interface component.

Example 15 is an extension of Example 14 or any other example disclosed herein, further comprising rotating the lock component in response to the user engaging the user interface component to allow movement of the slide insert component and the slide retract component toward the second end of the rail housing component.

Example 16 is an extension of Example 15 or any other example disclosed herein, further comprising driving the slide insert component and the slide retract component in the first direction by retraction of an extension spring positioned between a hard stop component and the slide insert component, the hard stop component coupled to the second end of the rail housing component.

Example 17 is an extension of Example 16 or any other example disclosed herein, further comprising coupling the slide insert component to the slide retract component by the tension lock component prior to the slide insert component reaching the second end of the rail housing component.

Example 18 is an extension of Example 17 or any other example disclosed herein, further comprising preventing the tension lock component from deflecting downward prior to the slide insert component reaching the second end of the rail housing component.

Example 19 is an extension of Example 18 or any other example disclosed herein, further comprising driving the slide retract component in the second, opposite direction from the second end of the rail toward the first end of the rail by a compression spring allowed to expand by the tension lock component deflecting downward.

Example 20 is an extension of Example 19 or any other example disclosed herein, further comprising restricting movement of the slide insert component and the cannula coupled to the slide insert component as the slide retract component and the needle move toward the first end of the rail housing component.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A needle mechanism module, comprising:
   a rail housing component;
   a slide insert component coupled to the rail housing component and configured to slide along the rail housing component;
   a slide retract component coupled to the rail housing component and configured to slide along the rail housing component;
   a hard stop component coupled to a first end of the rail housing component, the slide insert component and the slide retract component positioned toward a second, opposite end of the rail housing component;
   an insert extension spring coupled to the hard stop component and to the slide insert component;
   a retract compression spring positioned between the slide insert component and the slide retract component;
   a tension lock component positioned through the slide insert component and the slide retract component and configured to couple the slide insert component to the slide retract component;
   an insert lock positioned against the slide insert component and configured to restrict movement of the slide insert component and the slide retract component toward the hard stop by the insert spring;
   a needle coupled to the slide insert component and the slide retract component, the needle further coupled to a liquid drug stored in a reservoir of a wearable drug delivery device; and
   a cannula surrounding a portion of the needle extending from the slide insert component, an end of the cannula coupled to the slide insert component.

2. The needle mechanism module of claim 1, further comprising a needle mechanism module lock coupled to the insert lock, the needle mechanism module lock configured to restrict movement of the insert lock.

3. The needle mechanism module of claim 2, wherein the needle mechanism module lock is coupled to a push button.

4. The needle mechanism module of claim 3, wherein the needle mechanism module is configured to remain in an idle state until a user engages the push button.

5. The needle mechanism module of claim 4, wherein the needle mechanism module lock is configured to allow movement of the insert lock responsive to the user engaging the push button.

6. The needle mechanism module of claim 5, wherein the insert lock is configured to rotate when allowed to move and to allow movement of the slide insert component and the slide retract component.

7. The needle mechanism module of claim 6, wherein the slide insert component and the slide retract component are configured to move along the rail housing component toward the hard stop component when allowed to move based on a force provided by the insert extension spring.

8. The needle mechanism module of claim 7, wherein the needle and the cannula are configured to move with the slide insert component and the slide retract component and are configured to be inserted into the user as the slide insert component and the slide retract component move toward the hard stop component.

9. The needle mechanism module of claim 8, wherein when the tension lock component meets the hard stop component, an end of the tension lock component positioned furthest from the hard stop component is configured to deflect downward to enable the retract compression spring to expand, wherein prior to the tension lock component meeting the hard stop component, a rail beam of the rail housing component is configured to prevent the end of the tension lock component from deflecting downward.

10. The needle mechanism of claim 9, wherein the needle is inserted into the user by a maximum amount when the tension lock component meets the hard stop component.

11. The needle mechanism module of claim 10, wherein the slide insert component and the cannula remain stationary and the slide retract component and the needle retract away from the hard stop component toward the second end of the rail housing component as the retract compression spring expands, thereby removing the needle from the user and leaving the cannula in the user.

12. A method, comprising:
    releasing a lock component;
    driving a slide insert component and a slide retract component in a first direction from a first end of a rail housing component to a second, opposite end of the rail housing component;
    inserting a needle and a cannula into a user as the slide insert component is driven toward the second end of the rail housing component, the needle and the cannula coupled to the slide insert component;
    deflecting a tension lock component positioned through the slide insert component and the slide retract component to allow a retract compression spring to expand;
    driving the slide retract component in a second, opposite direction from the second end of the rail housing component toward the first end of the rail housing component; and
    removing the needle from the user while the cannula remains inserted in the user.

13. The method of claim 12, further comprising restricting movement of the slide insert component and the slide retract component toward the second end of the rail housing component prior to releasing the lock component.

14. The method of claim 13, further comprising releasing the lock component in response to the user engaging a user interface component.

15. The method of claim 14, further comprising rotating the lock component in response to the user engaging the user interface component to allow movement of the slide insert component and the slide retract component toward the second end of the rail housing component.

16. The method of claim 15, further comprising driving the slide insert component and the slide retract component in the first direction by retraction of an extension spring positioned between a hard stop component and the slide insert component, the hard stop component coupled to the second end of the rail housing component.

17. The method of claim 16, further comprising coupling the slide insert component to the slide retract component by the tension lock component prior to the slide insert component reaching the second end of the rail housing component.

18. The method of claim 17, further comprising preventing the tension lock component from deflecting downward prior to the slide insert component reaching the second end of the rail housing component.

19. The method of claim 18, further comprising driving the slide retract component in the second, opposite direction from the second end of the rail housing component toward the first end of the rail housing component by a compression spring allowed to expand by the tension lock component deflecting downward.

20. The method of claim 19, further comprising restricting movement of the slide insert component and the cannula coupled to the slide insert component as the slide retract component and the needle move toward the first end of the rail housing component.

* * * * *